(12) United States Patent
Sternby

(10) Patent No.: US 11,083,828 B2
(45) Date of Patent: Aug. 10, 2021

(54) APPARATUS FOR EXTRACORPOREAL BLOOD TREATMENT

(71) Applicant: GAMBRO LUNDIA AB, Lund (SE)

(72) Inventor: Jan Sternby, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 536 days.

(21) Appl. No.: 15/773,668

(22) PCT Filed: Nov. 8, 2016

(86) PCT No.: PCT/EP2016/076911
§ 371 (c)(1),
(2) Date: May 4, 2018

(87) PCT Pub. No.: WO2017/080969
PCT Pub. Date: May 18, 2017

(65) Prior Publication Data
US 2018/0333526 A1 Nov. 22, 2018

(30) Foreign Application Priority Data

Nov. 9, 2015 (SE) .................................. 1551446-6

(51) Int. Cl.
*A61M 1/16* (2006.01)
*A61M 1/36* (2006.01)
*A61M 1/34* (2006.01)

(52) U.S. Cl.
CPC ............ *A61M 1/1607* (2014.02); *A61M 1/16* (2013.01); *A61M 1/1611* (2014.02);
(Continued)

(58) Field of Classification Search
CPC ...... A61M 1/1607; A61M 1/16; A61M 1/341; A61M 1/3413; A61M 1/3653;
(Continued)

(56) References Cited

U.S. PATENT DOCUMENTS

| 5,900,136 A | 5/1999 | Gotsu et al. |
| 5,938,938 A | 8/1999 | Bosetto et al. |

(Continued)

FOREIGN PATENT DOCUMENTS

| EP | 0547025 | 6/1993 |
| EP | 0920877 | 6/1999 |

(Continued)

OTHER PUBLICATIONS

International Search Report—PCT/EP2016/076911 dated Jan. 30, 2017—5 pages.

(Continued)

*Primary Examiner* — Tatyana Zalukaeva
*Assistant Examiner* — Jessica R Arble
(74) *Attorney, Agent, or Firm* — K&L Gates LLP

(57) ABSTRACT

An extracorporeal blood treatment apparatus is provided comprising a filtration unit (2) connected to a blood circuit (17) and to a dialysis fluid circuit (32), a preparation device (9) for preparing and regulating the composition of the dialysis fluid; a control unit (12) is configured for determining or receiving a proposed value ($Cond_{prop}$) of a conductivity for the dialysis fluid in the dialysis supply line (8) and to determine a set value ($Cond_{set}$) for the conductivity in the dialysis fluid as a function of the proposed value ($Cond_{prop}$) and as a function of at least one of a second parameter (UF volume/W; WL/W) indicative of a patient fluid overload and a third parameter ($g_{conc}$) chosen in the group including: a glucose concentration in the patient and a concentration-related parameter of at least glucose in the patient.

28 Claims, 1 Drawing Sheet

(52) U.S. Cl.
CPC .......... *A61M 1/341* (2014.02); *A61M 1/3413* (2013.01); *A61M 1/3609* (2014.02); *A61M 1/3653* (2013.01); *A61M 2205/3317* (2013.01); *A61M 2230/201* (2013.01); *A61M 2230/65* (2013.01)

(58) Field of Classification Search
CPC .............. A61M 1/1611; A61M 1/3609; A61M 2230/65; A61M 2205/3317; A61M 2230/201
See application file for complete search history.

(56) References Cited

U.S. PATENT DOCUMENTS

| | | | |
|---|---|---|---|
| 6,110,384 | A | 8/2000 | Goux et al. |
| 2010/0298751 | A1* | 11/2010 | Schulte ............... A61M 1/1609 604/4.01 |
| 2014/0074008 | A1 | 3/2014 | Fontanazzi et al. |
| 2014/0077483 | A1* | 3/2014 | Jolda ....................... B60R 22/48 280/801.1 |
| 2014/0088483 | A1* | 3/2014 | Fontanazzi .......... A61M 1/1605 604/6.09 |

FOREIGN PATENT DOCUMENTS

| | | |
|---|---|---|
| EP | 2 377 563 | 10/2011 |
| EP | 2 745863 | 6/2014 |
| GB | 2 052 303 | 1/1981 |
| WO | WO-2014045224 A1 * | 3/2014 .......... A61M 1/3687 |

OTHER PUBLICATIONS

International Type Search Report—SE Application 1551446-6 dated Apr. 21, 2016—5 pages.
Written Opinion of the International Searching Authority PCT/EP2016/076911—8 pages.

* cited by examiner

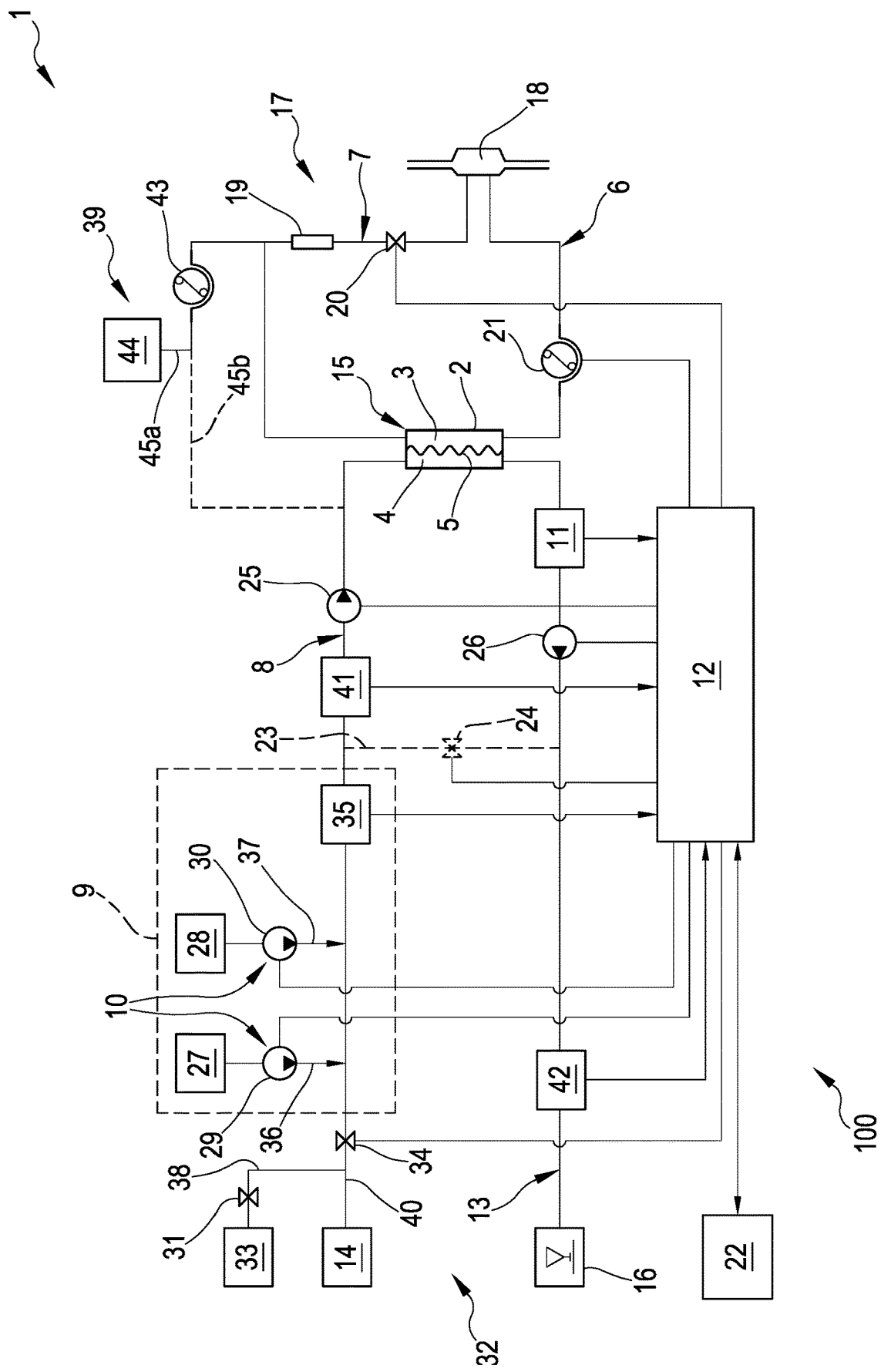

APPARATUS FOR EXTRACORPOREAL BLOOD TREATMENT

PRIORITY CLAIM

The present application is a National Stage of International Application No. PCT/EP2016/076911, filed Nov. 8, 2016, which claims priority to Swedish Patent Application No. 1551446-6, filed Nov. 9, 2015, the entire contents of each of which are incorporated herein by reference and relied upon.

TECHNICAL FIELD

The present invention relates to an apparatus for extracorporeal blood treatment and a method for controlling the extracorporeal blood treatment apparatus.

In particular, the invention may be used for regulating the conductivity of a dialysis liquid during a hemodialysis or hemodiafiltration treatment.

In more detail, the apparatus and the method are particularly adapted for regulating the proper concentration of sodium in the dialysis liquid, particularly to run a physiological isotonic or isonatremic or isonatrikalemic dialysis treatment.

The apparatus and the method herewith provided are suitable for regulating the dialysis fluid sodium concentration taking into account of 'artificially' low values of plasma conductivity for isotonic or isonatremic or isonatrikalemic dialysis treatment.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids (phosphates, monosodium acids) and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45).

In order to overcome renal dysfunction, resort is conventionally made to a blood treatment involving extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the dialyzer which are delimited by the semipermeable membrane, so that a fraction of the plasma fluid passes by ultrafiltration through the membrane into the compartment containing the dialysis liquid.

The blood treatment which takes place in a dialyzer as regards waste from the metabolism and electrolytes results from two mechanisms of molecular transport through the membrane.

On the one hand, the molecules migrate from the liquid where their concentration is higher to the liquid where their concentration is lower. This is diffusive transport.

On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodialysis).

Moreover, sodium is the main ionic solute of extracellular volume. From literature search and according to the main opinion leaders in the dialysis field, the determination of dialysis fluid sodium concentration to be used during the dialysis treatment appears as one of the major challenges of dialysis prescription.

The dialysis fluid sodium concentration significantly affects the sodium balance and the intracellular hydration of the patient with implications on hemodialysis tolerance and also long term patient survival.

Hypertonic dialysis fluid sodium prescription will result in a positive sodium balance followed by a water shift from the intracellular to extracellular compartment. The intracellular dehydration increases vasopressin release and provokes thirst with the consequence of a greater inter-dialytic weight gain and hypertension.

On the contrary, a dialysis fluid sodium concentration that is too low (i.e., hypotonic) will provoke a negative sodium gradient with a water shift in the intracellular compartment, which is responsible for intra-dialytic cramps, headache, hypovolemia and risk of hypotension.

One of current opinions is the idea that sodium balance should be maintained substantially null during a dialysis treatment: this is based on the so-called "sodium set point" theory, according to which both healthy subjects and dialysis patients tend to maintain a stable extra-cellular sodium concentration.

As above mentioned, sodium is removed during dialysis through convection and diffusion. The main sodium removal process during dialysis is convective. If we assume that the ultrafiltrate fluid is basically isotonic, convection does not change the tonicity of the extracellular fluid.

There is a need to help the physician to prescribe a correct and "physiological" dialysis fluid composition to treat the patient.

Moreover, a second need is to have a bio-sensing-based therapy which is easy to use and designed also for operators not very skilled or working in crowded and very busy dialysis rooms.

To at least partly solve the above mentioned drawbacks, document U.S. Pat. No. 4,508,622 teaches a dialysis device in which the electrolyte composition of the untreated and treated fluids routed through the dialyzer may be determined and the composition of the dialysis solution adapted to the patient's requirements.

A first electrolyte detector (conductivity cell) is provided upstream of the dialyzer and a second electrolyte detector (conductivity cell) is provided downstream of the dialyzer. Each detector is coupled to a readout element through which both of the values of the dialysis solution may be observed and eventually controlled. In more detail, the apparatus according to U.S. Pat. No. 4,508,622 consists essentially of a unit for production of the dialysis solution and a dialyzer connected to the unit and followed downstream by a pump to produce a vacuum in the dialyzer on the side of the dialysis fluid. The detector mounted upstream of the dialyzer, and connected with a control unit, measures the conductivity of the total dialysis solution.

A second detector is mounted downstream of dialyzer and is connected with a comparator which is, in turn, connected to a differentiation unit. A control signal is provided by the differentiation unit to control unit if there is a difference in the differentiation unit that deviates from the predetermined nominal value.

During dialysis fluid circulation, if detector generates a signal to the evaluation unit and subsequently to the differentiation unit which deviates by a certain amount from the signal generated by detector, i.e., a difference in value appears which deviates from the predetermined value for differentiation unit, the difference unit activates the control unit, which in turn switches concentrate pump on or off as a function of the higher or lower concentration in the dialysis solution to be produced. A treatment in which the dialysis fluid has the same conductivity of the blood and of the spent dialysis fluid, is one of the described implementations.

However, the dialysis fluid and the blood reach the same conductivity after a certain time lapse which clearly affects the pre-dialytic plasma sodium content. Therefore, the method described in U.S. Pat. No. 4,508,622 in not properly an 'isoconductive' dialysis treatment.

In any case, 'isoconductive' dialysis has been shown to lead to undesired sodium loading in the patient.

Moreover, the prior art devices include dialysis apparatus wherein the conductivity of dialysis fluid is controlled in order to reach a desired post-dialysis plasmatic conductivity, i.e. conductivity (or sodium concentration) of the patient's blood at the end of the dialysis treatment.

It is known, for example from EP 1389475, a dialysis apparatus provided with a conductivity system that computes the dialysis fluid conductivity (corresponding to the dialysis fluid sodium concentration) from periodic measurements of the sodium blood concentration allowing the sodium level of the patient to reach a prescribed end-of-session value.

This dialysis apparatus includes a bag and a pump for infusing a patient with an infusion solution containing sodium at a determined and known concentration.

A structure for determining the sodium concentration $[Na^+]_{dial}$ of the dialysis liquid is also provided so that the patient's body tends towards a desired sodium concentration $[Na^+]_{des}$, as a function of the dialysance D for sodium of the dialyzer, of the desired sodium concentration $[Na^+]_{des}$ inside the patient's body, of the infusion flow rate and of the sodium concentration $[Na^+]_{sol}$ of the infusion solution.

A control unit drives the pump for regulating the sodium concentration of the dialysis liquid such that this concentration is equal (tends towards) to the determined concentration $[Na^+]_{dial}$.

As previously mentioned, one of the problems of the dialysis apparatus of the discussed prior art is presently the choice of the appropriate post-dialysis plasmatic conductivity target.

With the methods described, for example in EP 547025 or in EP 920877, it is possible to determine the plasma conductivity and thereby to properly regulate the dialysis fluid preparation section.

The described system however changes the blood conductivity and tonicity since the dialysis fluid enters into contact and exchange significantly with blood before a plasma conductivity calculation; the effect on plasma conductivity is in an amount proportional to the difference between blood and dialysis fluid conductivities.

Document U.S. Pat. No. 8,182,692 describes a dialysis apparatus providing a treatment in which a dialysis fluid having a sodium concentration substantially equal to the estimated current sodium concentration in the patient's blood is performed by placing the dialysis fluid in communication with the patient's blood across the semi-permeable membrane to perform a dialysis treatment on the patient's blood without substantially altering the sodium concentration of the patient's blood during the performance of the dialysis treatment.

In more detail, a solution supply device, containing a conductivity-testing solution, is selectively placed in communication with dialyzer and the blood flowing therein.

According to this patent, any subject, including hemodialysis patients, has a set level of sodium in his body, referred to as the "set point." The set point of a subject tends to remain relatively constant, and sodium levels deviating too far from the set point may cause discomfort to the subject. Given the above, the method of the prior art includes causing blood to flow through blood conduit of the dialyzer and flowing the conductivity-testing solution in the opposite direction through the dialyzer.

Conductivity detectors measure the conductivity of conductivity-testing solution as the solution enters and exits dialyzer. Conductivity-testing solution is formulated such that electrically conductive solutes other than sodium in the patient's blood have little or no effect on the conductivity measurements of conductivity-testing solution.

According to U.S. Pat. No. 8,182,692, due to the closely matched concentrations of electrically conductive solutes, such as phosphate, sulfate, bicarbonate, potassium, calcium, and magnesium, in conductivity-testing solution and in the patient's blood, little diffusion of those electrically conductive solutes occurs across membrane. Consequently, the conductivity measurement of conductivity-testing solution is closely correlated with the level of sodium in the patient's blood.

Therefore, conductivity-testing solution is exclusively used to accurately determine the level of sodium in the patient's blood as a function of the change in conductivity across dialyzer of the conductivity-testing solution.

Control unit then determines the level of sodium in the patient's blood as a function of the measured conductivity values.

After determining the concentration of sodium in the patient's blood, dialysis fluid may be prepared to include a concentration of sodium that is substantially equal to the concentration of sodium determined to exist in the patient's blood.

Moreover, US2012/018379 discloses an apparatus and a method for the determination and regulation of the concentration of one dissolved substance (e.g. sodium) in a dialysis fluid circuit of a hemodialysis machine.

The user presets the sodium regulation range before the start of the dialysis using an estimated value for the dialysis fluid sodium required to achieve the isonatremic state or a lab measurement of the patient sodium or a value determined by the regulation from earlier treatments. In addition, the distribution volume of the patient is input for the application of the model for the correction of the diffusive balance. Furthermore, the initial concentrations of bicarbonate and potassium in the patient are set. They come from an analysis by means of a blood gas analyzer before the start of the dialysis treatment.

After the start of the treatment, the dialysis fluid flow and the conductivity are determined upstream and downstream of the dialyzer and a calculation of the updated current bicarbonate and potassium concentration in the patient takes place with it being assumed that the potassium clearance corresponds to the sodium clearance and that the bicarbonate clearance corresponds to 70% of the sodium clearance. The sodium clearance from the blood flow is estimated until the presence of the first clearance measurement.

The calculation of the conductivity balance and of the correction term for the ion exchange and thus for the sodium balance then takes place from these data.

The conductivity of fluids measured upstream and downstream, the sodium balance and the correction term for the dialysate conductivity downstream of the dialyzer are then the input values for the sodium regulation. The desired conductivity thus determined is finally converted into a desired value for the dialysis fluid sodium while taking account of the composition of the dialysis concentrate and this preset value is transmitted to a metering unit for dialysis fluid preparation.

Notably, patients' plasma sodium vary considerably, both between patients and within a single patient. Indeed, for a big patient group, the average pre-dialysis plasma sodium concentration is approximately 138 mmol/l. However, patients may have pre-dialysis plasma sodium in the range 130-143 mmol/l (or even lower or higher). Presently, a problem with isonatremic (or isotonic, or isonatrikalemic) treatments is that the pre-dialysis value of sodium or plasma conductivity may be artificially low if the patient is fluid overloaded. This may also happen in diabetics who come in for treatment with high glucose values. The plasma conductivity may then be controlled to a too low value, and this may lead to cramps, nausea and other symptoms, and hypotensive episodes may occur that are both detrimental to the patient and labor intensive for the staff.

Finally, EP 2377563 discloses a dialysis apparatus comprising a blood treatment unit with an online preparation device for preparing a dialysis fluid containing sodium and comprising a dialysis preparation section for regulating the concentration of sodium in the dialysis fluid. The blood circuit is configured to circulate extracorporeal blood through the blood chamber; control means determines a value representative of the sodium concentration in the blood and are programmed for driving the dialysis preparation section as a function of the determined plasma sodium value, such that the substance concentration in the dialysis fluid tends towards: (i) the determined concentration of said substance in the blood if the determined concentration of said substance in the blood is greater than a minimum threshold and less than a maximum threshold; (ii) the minimum threshold if the determined concentration of said substance in the blood is less than the minimum threshold; (iii) the maximum threshold if the determined concentration of said substance in the blood is greater than the maximum threshold.

The plasma sodium content is determined by measuring the inlet and outlet conductivities of the dialysis fluid upstream and downstream the dialyzer, by then changing the conductivity upstream the filter by a prefixed step and measuring a second time the inlet and outlet conductivities of the dialysis fluid upstream and downstream the dialyzer with the modified conductivity value.

SUMMARY

A general aim of the present invention is providing an extracorporeal blood treatment apparatus able to automatically perform a proper setting of the dialysis fluid content of a substance, particularly an ionic substance, present in the blood as well.

In detail it is an aim of the present invention to provide an extracorporeal blood treatment apparatus with a proper tool helping the physician to prescribe a "physiological" dialysis fluid composition, particularly to safely run an isotonic, isonatremic or isonatrikalemic dialysis treatment.

It is an aim of the present invention to provide an extracorporeal blood treatment apparatus configured for identifying cases for which isotonic, isonatremic or isonatrikalemic dialysis treatments may not be the best treatment option providing a corresponding more physiological set value for the dialysis fluid conductivity by either setting a substance concentration (e.g. sodium) or setting a conductivity in the dialysis fluid.

In this respect, the present invention aims at modifying the conductivity set point, taking into account the patient fluid overload and, e.g., a prescribed volume to be removed during the treatment. Alternatively, or additionally, the present invention aims at modifying the conductivity set point, taking into account an estimated or measured glucose level in diabetic patients.

A further aim of the invention is to make available an extracorporeal blood treatment apparatus provided with a selectable biosensing-based therapy which is easy to use and designed for not skilled operators or users working in crowded and busy dialysis rooms.

It is an aim of the invention to provide an extracorporeal blood treatment machine configured to automatically perform a proper automatic setting of the dialysis fluid conductivity or dialysis fluid substance (e.g. sodium) concentration.

A further aim of the invention is to make available a dialysis apparatus able to provide an automated delivery and control of the dialysis prescription, particularly in order to restore at each dialysis session the proper sodium-water equilibrium to the patient.

At least one of the above-indicated aims is attained by an apparatus and a corresponding method as in one or more of the appended claims, taken singly or in any combination.

According to a first independent aspect an apparatus for extracorporeal blood treatment is provided, comprising:
  a filtration unit (2) having a primary chamber (3) and a secondary chamber (4) separated by a semi-permeable membrane (5);
  a blood withdrawal line (6) connected to an inlet of the primary chamber (3),
  a blood return line (7) connected to an outlet of the primary chamber (3), said blood lines being configured for connection to a patient cardiovascular system;
  a dialysis supply line (8) connected to an inlet of the secondary chamber (4);
  a dialysis effluent line (13) connected to an outlet of the secondary chamber (4);
  a preparation device (9) for preparing a dialysis fluid connected to said supply line (8) and comprising regulating means (10) for regulating the composition of the dialysis fluid,
  a control unit (12) connected to the regulating means (10) and programmed for
    obtaining a proposed value ($Cond_{prop}$) of a first parameter for the dialysis fluid in the dialysis supply line (8), the first parameter being chosen in the group including a conductivity for the dialysis fluid, a conductivity-related parameter for the dialysis fluid, a concentration of at least a substance for the dialysis fluid, a concentration-related parameter of at least a substance for the dialysis fluid, obtaining a value for a second parameter, the second parameter being related to a patient fluid overload; and/or obtaining a value for a third parameter, the third parameter being chosen in the group including:
a non-ionic substance concentration in the patient;
a concentration-related parameter of at least a non-ionic substance in the patient;

determining a set value ($Cond_{set}$) for the first parameter as a function of the proposed value ($Cond_{prop}$) for the first parameter and of at least one of the second and third parameter.

According to a second independent aspect a method for setting parameters in an apparatus for extracorporeal blood treatment is provided, the apparatus comprising:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis supply line (8) connected to an inlet of the secondary chamber (4);

a dialysis effluent line (13) connected to an outlet of the secondary chamber (4);

a preparation device (9) for preparing a dialysis fluid connected to said supply line (2) and comprising regulating means (10) for regulating the composition of the dialysis fluid, a control unit (12) connected to the regulating means (10) and programmed for obtaining a proposed value ($Cond_{prop}$) of a first parameter for the dialysis fluid in the dialysis supply line (8), the first parameter being chosen in the group including a conductivity for the dialysis fluid, a conductivity-related parameter for the dialysis fluid, a concentration of at least a substance for the dialysis fluid, a concentration-related parameter of at least a substance for the dialysis fluid, the method comprising the following steps performed by the control unit:

obtaining the proposed value ($Cond_{prop}$) of the first parameter for the dialysis fluid in the dialysis supply line (8), obtaining a value for a second parameter, the second parameter being related to a patient fluid overload; and/or obtaining a value for a third parameter, the third parameter being chosen in the group including:
a non-ionic substance concentration in the patient;
a concentration-related parameter of at least a non-ionic substance in the patient;

determining a set value ($Cond_{set}$) for the first parameter as a function of the proposed value ($Cond_{prop}$) for the first parameter and at least one of the second and third parameter.

In a 3$^{rd}$ aspect according to anyone of the previous aspects, the second parameter is indicative of a patient fluid overload.

In a 4$^{th}$ aspect according to anyone of the previous aspects, the second parameter is chosen in the group including:
a weight loss (WL) for the patient;
a weight loss-related parameter;
a weight loss rate (WLR) for the patient;
an ultrafiltration volume (UF volume);
an ultrafiltration volume-related parameter;
an ultrafiltration rate (UFR);
an absolute blood volume;
a ratio between an absolute blood volume and a weight (W) of the patient;
a blood volume variation;
a refilling index (RI) for the patient;
a ratio between an ultrafiltration volume (UF volume) and a weight (W) of the patient;
a ratio between a weight loss (WL) for the patient and a weight (W) of the patient;
a difference between an overloaded weight of the patient and a non-overloaded weight for the patient.

In a 5$^{th}$ aspect according to anyone of the previous aspects, the third parameter is chosen in the group including:
a glucose concentration ($g_{conc}$) in the patient;
a concentration-related parameter of at least glucose in the patient.

In a 6$^{th}$ aspect according to anyone of the previous aspects, the control unit (12) is configured to determine the set value ($Cond_{set}$) for the first parameter as a linear function of the second parameter.

In a 7$^{th}$ aspect according to anyone of the previous aspects, the control unit (12) is configured to determine the set value ($Cond_{set}$) for the first parameter as a linear function of the third parameter.

In an 8$^{th}$ aspect according to anyone of the previous aspects, the control unit (12) is configured to determine the set value ($Cond_{set}$) for the first parameter as a function of at least the second parameter and the third parameter.

In a 9$^{th}$ aspect according to anyone of the previous aspects, the control unit (12) is configured to determine the set value ($Cond_{set}$) for the first parameter as a weighted function of the second parameter:

$$Cond_{set} = \beta_1 \cdot \text{second parameter} + \text{offset}$$

optionally wherein $\beta_1$ and offset are respective constants.

In a 10$^{th}$ aspect according to anyone of the previous aspects, the control unit (12) is configured to determine the set value ($Cond_{set}$) for the first parameter as a weighted function of the third parameter:

$$Cond_{set} = \beta_2 \cdot \text{third parameter} + \text{offset}$$

optionally wherein $\beta_2$ and offset are respective constants.

In a 11$^{th}$ aspect according to anyone of the previous aspects, the control unit (12) is configured to determine the set value ($Cond_{set}$) for the first parameter according to the following mathematical relationship:

$$Cond_{set} = Cond_{prop} + \beta_1 \cdot \text{second parameter} + \text{offset}$$

wherein $Cond_{prop}$ is the proposed value for the first parameter for the dialysis fluid in the dialysis supply line (8), optionally $\beta_1$ being a constant, offset being in particular an additional constant.

In a 12$^{th}$ aspect according to anyone of the previous aspects, the control unit (12) is configured to determine the set value ($Cond_{set}$) for the first parameter according to the following mathematical relationship:

$$Cond_{set} = Cond_{prop} + \beta_2 \cdot \text{third parameter} + \text{offset}$$

wherein $Cond_{prop}$ is the proposed value for the first parameter for the dialysis fluid in the dialysis supply line (8), optionally $\beta_2$ being a constant, offset being in particular an additional constant.

In a 13$^{th}$ aspect according to anyone of the previous aspects, the control unit (12) is configured to determine the set value ($Cond_{set}$) for the first parameter according to the following mathematical relationship:

$$Cond_{set} = Cond_{prop} + \beta_1 \cdot \text{second parameter} + \beta_2 \cdot \text{third parameter} + \text{offset}$$

wherein $Cond_{prop}$ is the proposed value for the first parameter for the dialysis fluid in the dialysis supply line (8), optionally $\beta_1$ and $\beta_2$ being respective constants, offset being in particular an additional constant.

In a 14$^{th}$ aspect according to anyone of the previous aspects, wherein the control unit (12) is configured to determine the set value ($Cond_{set}$) for the first parameter as an algebraic sum of at least a first term and a second term, the first term being function of the proposed value ($Cond_{prop}$), and in particular being equal to the proposed value ($Cond_{prop}$), the second term being function of at least one of the second and third parameter, in particular the control unit (12) being configured to determine the set value ($Cond_{set}$) as an algebraic sum of at least three terms, the third term being function of the other of said second and third parameter.

In a 15$^{th}$ aspect according to the previous aspect, the second term and/or the third term has a positive value.

In a 16$^{th}$ aspect according to anyone of the previous aspects, the first parameter is the conductivity for the dialysis fluid in the dialysis supply line (8).

In a 17$^{th}$ aspect according to anyone of the previous aspects, the second parameter is the relative weight loss (WL/W) for the patient.

In an 18$^{th}$ aspect according to anyone of the previous aspects, the third parameter is the glucose concentration ($g_{conc}$) in the patient.

In a 19$^{th}$ aspect according to anyone of the previous aspects, the control unit (12) is configured to determine the set value ($Cond_{set}$) for the conductivity as a weighted function of the second parameter, the second parameter being the relative weight loss (WL/W) or the relative ultrafiltration volume (UFvolume/W):

$$Cond_{set} = \beta_1 \cdot \frac{UFvolume}{W} + offset$$

or $$Cond_{set} = \beta_1 \cdot \frac{WL}{W} + offset$$

wherein $\beta_1$ is a constant chosen in the range:
 0 to 25: $0<\beta_1<25$; in particular included in the range between 0 to 12.5: $0<\beta_1\leq12.5$ in case the first parameter is conductivity and $\beta_1$ is referred to WL/W, $\beta_1$ unit being mS/cm;
 0 to 250: $0<\beta_1<250$; in particular included in the range between 0 to 125: $0<\beta_1\leq125$ in case the first parameter is concentration and $\beta_1$ is referred to WL/W, $\beta_1$ unit being mmol/L;
 corresponding to the above in the case where the second parameter is different from WL/W, for example WL, then $\beta_1$ is a constant chosen in the range:
UFvolume [L] is the ultrafiltration volume;
WL [Kg] is the weight loss;
W [Kg] is the patient weight; and
offset being a constant, different from zero.

In a 20$^{th}$ aspect according to anyone of the previous aspects, the control unit (12) is configured to determine the set value ($Cond_{set}$) for the conductivity as a weighted function of the third parameter, the third parameter being the glucose concentration ($g_{conc}$):

$$Cond_{set} = \beta_2 \cdot g_{conc} + offset$$

wherein $\beta_2$ is a constant chosen in the range:
 0 to 0.2: $0<\beta_2<0.2$, in particular included in the range between 0.05 to 0.15: $0.05\leq\beta_2\leq0.15$ in case the first parameter is conductivity, $\beta_2$ unit being $$\left[\frac{mS/cm}{g/L}\right];$$

0 to 2: $0<\beta_2<2$, in particular included in the range between 0.5 to 1.5: $0.5\leq\beta_2\leq1.5$ in case the first parameter is concentration, $\beta_2$ unit being $$\left[\frac{mmol}{g}\right];$$

offset being a constant, different from zero.

In a 21$^{st}$ aspect according to anyone of the previous aspects, wherein the control unit (12) is configured to determine the set value ($Cond_{set}$) for the first parameter according to the following mathematical relationship:

$$Cond_{set} = Cond_{prop} + \beta_1 \cdot \frac{UFvolume}{W} + \beta_2 \cdot g_{conc} + offset$$

or $$Cond_{set} = Cond_{prop} + \beta_1 \cdot \frac{WL}{W} + \beta_2 \cdot g_{conc} + offset$$

wherein $Cond_{prop}$ is the proposed value for the first parameter for the dialysis fluid in the dialysis supply line (8);
UF volume [L] is the ultrafiltration volume;
WL [Kg] is the weight loss;
W [Kg] is the patient weight;
$g_{conc}$ [g/L] is the glucose concentration;
optionally wherein $\beta_1$ is a constant chosen in the range:
 0 to 25: $0<\beta_1<25$; in particular included in the range between 0 to 12.5: $0<\beta_1\leq12.5$ in case the first parameter is conductivity and $\beta_1$ is referred to WL/W, $\beta_1$ unit being mS/cm;
 0 to 250: $0<\beta_1<250$; in particular included in the range between 0 to 125: $0<\beta_1\leq125$ in case the first parameter is concentration and $\beta_1$ is referred to WL/W, $\beta_1$ unit being mmol/L;
 corresponding to the above in the case where the second parameter is different from WL/W, for example WL, then $\beta_1$ is a constant chosen in the range:
 0 to 0.3: $0<\beta_1<0.3$; in particular included in the range between 0 to 0.15: $0<\beta_1\leq0.15$ in case the first parameter is conductivity and $\beta_1$ is referred to WL, $\beta_1$ unit being mS/cm/kg;
 0 to 3: $0<\beta_1<3$; in particular included in the range between 0 to 1.5: $0<\beta_1\leq1.5$ in case the first parameter is concentration and $\beta_1$ is referred to WL, $\beta_1$ unit being mmol/L/kg;

and
optionally wherein $\beta_2$ is a constant chosen in the range:
 0 to 0.2: $0<\beta_2<0.2$, in particular included in the range between 0.05 to 0.15: $0.05\leq\beta_2\leq0.15$ in case the first parameter is conductivity, $\beta_2$ unit being $\left[\frac{mS/cm}{g/L}\right]$;

0 to 2: $0<\beta_2<2$, in particular included in the range between 0.5 to 1.5: $0.5 \leq \beta_2 \leq 1.5$ in case the first parameter is concentration, $\beta_2$ unit being $\left[\frac{mmol}{g}\right]$;

offset being a constant.

In a 22$^{nd}$ aspect according to anyone of the previous aspects, in case the set value (Cond$_{set}$) for the first parameter determined by the control unit (12) is lower than a lower limit for the first parameter, the set value (Cond$_{set}$) is set at a value equal to the lower limit; and/or in case the set value (Cond$_{set}$) for the first parameter determined by the control unit (12) exceeds an upper limit for the first parameter, the set value (Cond$_{set}$) is set at a value equal to the upper limit.

In a 23$^{rd}$ aspect according to anyone of the previous aspects, the control unit (12) is configured to determine the set value (Cond$_{set}$) for the first parameter as a function of the proposed value (Cond$_{prop}$) for the first parameter and of the third parameter, said third parameter being an estimated glucose concentration (g$_{conc}$) chosen in the group including:
  an average pre-dialysis glucose concentration for the patient;
  a predetermined set value for glucose concentration.

In a 24$^{th}$ aspect according to anyone of the previous aspects, the first parameter is the concentration of at least a substance in the dialysis fluid, said substance being in particular sodium.

In a 25$^{th}$ aspect according to anyone of the previous aspects, the control unit drives the regulating means (10) for regulating the conductivity or the concentration of at least a substance in the dialysis fluid, the control unit setting the first parameter value for the dialysis fluid in the dialysis supply line (8) at the calculated set value of the first parameter.

In a 26$^{th}$ aspect according to anyone of the previous aspects, the first parameter is the conductivity of the dialysis fluid, the proposed value for the first parameter being the conductivity set point for running an isoconductive dialysis, or an isotonic dialysis, or isonatremic dialysis, or an isonatrikalemic dialysis.

In a 27$^{th}$ aspect according to anyone of the previous aspects, the first parameter is the concentration of at least a substance in the dialysis fluid, the proposed value for the first parameter being the substance concentration set point for running an isoconductive dialysis, or an isotonic dialysis, or isonatremic dialysis, or an isonatrikalemic dialysis.

In a 28$^{th}$ aspect according to anyone of the previous aspects, the first parameter is the conductivity of the dialysis fluid, the proposed value for the first parameter being function of or equal to a plasma conductivity value; alternatively, the first parameter being the concentration of at least a substance in the dialysis fluid, the proposed value for the first parameter being function of or equal to a plasma sodium concentration value.

In a 29$^{th}$ aspect according to anyone of the previous aspects, the control unit (12) is configured for either calculating the proposed value for the first parameter or receiving the proposed value as an input.

In a 30$^{th}$ aspect according to anyone of the previous aspects, the control unit (12) is configured for calculating the proposed value for the first parameter as a function of a main contribution term based on a plasma conductivity, a plasma conductivity-related parameter, a concentration of at least a substance in the blood, a concentration-related parameter of at least a substance in the blood and as a function of an adjustment contribution term based on a concentration of at least a substance in the dialysis fluid chosen in the group including bicarbonate, potassium, acetate, lactate, citrate, magnesium, calcium, sulphate and phosphate.

In a 31$^{st}$ aspect according to the previous aspect, the control unit is configured to calculate the adjustment contribution term based on the concentration of two or more substances in the dialysis fluid chosen in the group including bicarbonate, potassium, acetate, lactate, citrate, magnesium, calcium, sulphate and phosphate, in particular as a function of the concentration of at least three of said substances, optionally as a function of the concentration of bicarbonate, potassium, acetate, and citrate in the dialysis fluid.

In a 32$^{nd}$ aspect according to anyone of the previous aspects 30 and 31, the control unit is configured to calculate the adjustment contribution term as a function of the weighted difference in concentration of at least a substance in the dialysis fluid and the same substance in the plasma, said substance being chosen in the group including bicarbonate, potassium, acetate, lactate and citrate, in particular as a function of the weighted difference in concentration of at least two of said substances, optionally as a function of the difference in concentration of bicarbonate, potassium, acetate, and citrate in the dialysis fluid and plasma.

In a 33$^{rd}$ aspect according to anyone of the previous aspects 30 to 32, the main contribution term is based on the plasma conductivity, or the concentration of at least a substance in the blood, and wherein the first parameter of the dialysis fluid is the conductivity of the dialysis fluid, or the concentration of at least a substance in the dialysis fluid, said substance being in particular sodium.

In a 34$^{th}$ aspect according to anyone of the previous aspects 30 to 33, the main contribution term is dimensionally a concentration of a substance in a fluid, particularly wherein the main contribution term is a dialysis fluid concentration of sodium at an isoconductive dialysis.

In a 35$^{th}$ aspect according to anyone of the previous aspects 30 to 34, the adjustment contribution term is the sodium concentration set point adjustment relative to the sodium concentration set point for the isoconductive dialysis, the adjustment contribution applied to the sodium concentration set point for the isoconductive dialysis provides a treatment chosen in the group including isotonic dialysis, isonatremic dialysis and isonatrikalemic dialysis.

In a 36$^{th}$ aspect according to anyone of the previous aspects 30 to 35, the adjustment contribution term is the sodium concentration set point adjustment relative to the sodium concentration set point for the isoconductive dialysis, the adjustment contribution applied to the sodium concentration set point for the isoconductive dialysis provides a treatment that removes from, or adds to, the plasma a defined amount of at least a substance.

In a 37$^{th}$ aspect according to anyone of the previous aspects 30 to 36, the control unit is configured to calculate the adjustment contribution term as a function of the molar conductivities of at least a substance in the dialysis fluid chosen in the group including sodium bicarbonate (NaHCO$_3$), sodium chloride (NaCl), sodium acetate (NaCH$_3$COO), potassium chloride (KCl), sodium lactate (NaC$_3$H$_5$O$_3$), and trisodium citrate (Na$_3$C$_6$H$_5$O$_7$), in particular as a function of the molar conductivities of at least two of said substances, in more detail as a function of the molar conductivities of at least three of said substances, optionally as a function of the molar conductivities of sodium bicarbonate ($NaHCO_3$), sodium chloride (NaCl), sodium acetate ($NaCH_3COO$), trisodium citrate ($Na_3C_6H_5O_7$) and potassium chloride (KCl).

In a $38^{th}$ aspect according to anyone of the previous aspects 30 to 37, the control unit is configured to calculate the adjustment contribution term as a function of a difference between a first molar conductivity of a substance chosen in the group including sodium bicarbonate ($NaHCO_3$), sodium acetate ($NaCH_3COO$), trisodium citrate ($Na_3C_6H_5O_7$), sodium lactate ($NaC_3H_5O_3$), potassium chloride (KCl), and a molar conductivity of sodium chloride (NaCl).

In a $39^{th}$ aspect according to anyone of the previous aspects 30 to 38, the control unit is configured to calculate the adjustment contribution term as a function of an estimated or measured plasma water concentration of at least a substance chosen in the group including bicarbonate, potassium, acetate, lactate and citrate, in particular as a function of the estimated or measured plasma water concentration of at least two of said substances, in more detail as a function of the estimated plasma water concentration of at least three of said substances, optionally as a function of the estimated plasma water concentration of bicarbonate, potassium and acetate.

In a $40^{th}$ aspect according to anyone of the previous aspects 30 to 39, the control unit is configured to calculate the adjustment contribution term as an algebraic sum of at least two components, a first component being function of the difference in concentration of at least a substance in the dialysis fluid and the same substance in the blood plasma, the second component being function of the weighted difference in concentration of at least a second substance in the dialysis fluid and the same second substance in the blood plasma, particularly wherein said substance is chosen in the group including bicarbonate anions ($HCO_3$), acetate anions ($CH_3COO^-$), citrate anions ($C_6H_5O_7^{3-}$), and potassium ions ($K^+$).

In a $41^{st}$ aspect according to anyone of the previous aspects 30 to 40, the control unit is configured to calculate the adjustment contribution term as an algebraic sum of at least two components, a first component being function of a concentration of at least a substance in the dialysis fluid and/or in the blood plasma, a second component being function of a concentration of at least a second substance in the dialysis fluid and/or in the blood plasma, particularly wherein said substance is chosen in the group including bicarbonate anions ($HCO_3^-$), acetate anions ($CH_3COO^-$), citrate anions ($C_6H_5O_7^{3-}$), and potassium ions ($K^+$).

In a $42^{nd}$ aspect according to anyone of the previous aspects 30 to 41, the control unit is configured to calculate the adjustment contribution term as a function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a $43^{rd}$ aspect according to anyone of the previous aspects, the control unit is further configured to obtain a plasma conductivity and in particular to calculate a plasma conductivity as a function of the dialysate flow rate at the outlet of the secondary chamber (4) and the blood flow rate in the blood lines (6, 7), the proposed value ($Cond_{prop}$) for the first parameter being function of the plasma conductivity.

In a $44^{th}$ aspect according to anyone of the previous aspects, the control unit is further configured to obtain a plasma conductivity and in particular to calculate a plasma conductivity as a function of at least an efficiency parameter of the filtration unit (2), in particular a clearance of the filtration unit (2), optionally the urea clearance, the proposed value ($Cond_{prop}$) for the first parameter being function of the plasma conductivity.

In a $45^{th}$ aspect according to anyone of the previous aspects, the control unit is further configured to obtain a plasma conductivity and in particular to calculate a plasma conductivity as a function of at least an initial conductivity of the dialysate and of at least a conductivity of the dialysis fluid in the dialysis supply line (8), the proposed value ($Cond_{prop}$) for the first parameter being function of the plasma conductivity.

In a $46^{th}$ aspect according to anyone of the previous aspects, the control unit is programmed to allow selection of at least one treatment mode chosen in the group including isotonic dialysis, isonatremic dialysis and isonatrikalemic dialysis, the control unit is configured to drive the regulating means as a function of the calculated set value ($Cond_{set}$) and of the chosen treatment mode to set either a desired dialysis fluid inlet conductivity or a desired dialysis fluid inlet substance concentration, in particular said substance being sodium.

In a $47^{th}$ aspect according to anyone of the previous aspects, the control unit (12) is further programmed for calculating a value representative of the parameter of the blood in said blood lines, the blood parameter being chosen in the group including a plasma conductivity, a plasma conductivity-related parameter, a concentration of at least a substance in the blood, a concentration-related parameter of at least a substance in the blood.

In a $48^{th}$ aspect according to anyone of the previous aspects, the control unit (12) is further programmed for receiving as an input a value representative of the parameter of the blood in said blood lines, the blood parameter being chosen in the group including a plasma conductivity, a plasma conductivity-related parameter, a concentration of at least a substance in the blood, a concentration-related parameter of at least a substance in the blood.

In a $49^{th}$ aspect according to anyone of the previous aspects, the control unit (12) is programmed for storing in a memory a value representative of the parameter of the blood in said blood lines, said value representative of the parameter of the blood being not calculated by the control unit, the blood parameter being chosen in the group including a plasma conductivity, a plasma conductivity-related parameter, a concentration of at least a substance in the blood, a concentration-related parameter of at least a substance in the blood.

In a $50^{th}$ aspect according to anyone of the previous aspects 30 to 42, the adjustment contribution term has a negative value.

In a $51^{st}$ aspect according to anyone of the previous aspects, the control unit is configured to calculate a plasma conductivity as a function of at least one flow rate, in particular said flow rate being chosen in the group including the dialysate flow rate at the outlet of the secondary chamber (4) and the blood flow rate in the blood lines (6, 7).

In a $52^{nd}$ aspect according to the previous aspect, the control unit is configured to calculate a plasma conductivity as a function of the dialysate flow rate at the outlet of the secondary chamber (4) and the blood flow rate in the blood lines (6, 7).

In a 53$^{rd}$ aspect according to anyone of the previous aspects, the control unit is configured to calculate a plasma conductivity as a function of at least an efficiency parameter of the filtration unit (2), in particular a clearance of the filtration unit (2), optionally the urea clearance.

In a 54$^{th}$ aspect according to anyone of the previous aspects, the control unit is configured to calculate a plasma conductivity as a function of at least an initial conductivity of the dialysate.

In a 55$^{th}$ aspect according to anyone of the previous aspects, the control unit is configured to calculate a plasma conductivity as a function of at least a conductivity of the dialysis fluid in the dialysis supply line (8).

In a 56$^{th}$ aspect according to anyone of the previous aspects, the control unit is configured to calculate a plasma conductivity according to the following formula (IV):

$$\kappa'_{p,1} = \kappa_{0,do} + \frac{Q_{do}}{Q_{Bset}}(\kappa_{0,do} - \kappa_{0,di}) \quad (IV)$$

wherein:

| | |
|---|---|
| $\kappa_{p,1}$ | Plasma conductivity first estimate; |
| $Q_{do}$ | Dialysate flow rate at the filtration unit outlet; |
| $Q_{bset}$ | Set blood flow rate or set blood water flow rate at the filtration unit inlet; |
| $\kappa_{0,di}$ | Dialysis fluid conductivity at the filtration unit inlet for a pure electrolyte solution; |
| $\kappa_{0,do}$ | Dialysate conductivity at the filtration unit outlet for a pure electrolyte solution; |

In a 57$^{th}$ aspect according to anyone of the previous aspects, the control unit is configured to calculate a plasma conductivity according to the following formula (V):

$$\kappa''_{p,1} = \kappa_{0,di} + \frac{Q_{do}}{K_u}(\kappa_{0,do} - \kappa_{0,di}) \quad (V)$$

wherein:

| | |
|---|---|
| $\kappa_{p,1}$ | Plasma conductivity first estimate; |
| $Q_{do}$ | Dialysate flow rate at the filtration unit outlet; |
| $K_u$ | Filtration unit clearance for urea; |
| $\kappa_{0,di}$ | Dialysis fluid conductivity at the filtration unit inlet for a pure electrolyte solution; |
| $\kappa_{0,do}$ | Dialysate conductivity at the filtration unit outlet for a pure electrolyte solution; |

In a 58$^{th}$ aspect according to anyone of the previous aspects, immediately after calculating an initial plasma conductivity, the control unit is configured to drive the regulating means (10) to change the composition of the dialysis fluid and to set the dialysis fluid conductivity substantially equal to the calculated plasma conductivity.

In a 59$^{th}$ aspect according to the previous aspect, after setting the dialysis fluid conductivity substantially equal to the calculated plasma conductivity, the control unit is configured to execute a second calculating step, based on a second determined initial conductivity of the dialysate and on a second corresponding conductivity of the dialysis fluid in the dialysis supply line (8), of a second estimate of the initial plasma conductivity, said calculating the second estimate being performed maintaining the dialysis fluid conductivity substantially constant and substantially equal to the calculated plasma conductivity.

In a 60$^{th}$ aspect according to anyone of the previous aspects, after calculating the second estimate of the initial plasma conductivity, the control unit is configured to drive the regulating means (10) to change the composition of the dialysis fluid and to set the dialysis fluid conductivity substantially equal to said second estimate.

In a 61$^{st}$ aspect according to anyone of the previous aspects, the control unit is programmed to allow selection of at least one treatment mode chosen in the group including isotonic dialysis, isonatremic dialysis and isonatrikalemic dialysis, the control unit is configured to drive the regulating means as a function of the calculated plasma conductivity and of the chosen treatment mode to set either a desired dialysis fluid inlet conductivity or a desired dialysis fluid inlet substance concentration, in particular said substance being sodium.

In a 62$^{nd}$ aspect according to the previous aspect, the control unit is programmed to keep the desired dialysis fluid inlet conductivity substantially constant throughout the remainder of the treatment.

Further characteristics and advantages of the present invention will better emerge from the detailed description that follows of at least an embodiment of the invention, illustrated by way of non-limiting example in the accompanying FIGURES of the drawings.

BRIEF DESCRIPTION OF THE DRAWINGS

The description will now follow, with reference to the appended FIGURES, provided by way of non-limiting example, in which:

FIG. 1 schematically represents an extracorporeal blood treatment apparatus made according to an illustrating embodiment.

DETAILED DESCRIPTION

FIG. 1 illustrates an extracorporeal blood treatment apparatus 1 in an embodiment of the invention.

An example of a hydraulic circuit 100 is schematically illustrated, but it is to be noted that the specific structure of the hydraulic circuit 100 is not relevant for the purposes of the present invention and therefore other and different circuits to those specifically shown in FIG. 1 might be used in consequence of the functional and design needs of each single medical apparatus.

The hydraulic circuit 100 exhibits a dialysis fluid circuit 32 presenting at least one dialysis fluid supply line 8, destined to transport a dialysis liquid from at least one source 14 towards a treatment station 15 where one or more filtration units 2, or dialyzers, operate.

The dialysis fluid circuit 32 further comprises at least one dialysis effluent line 13, destined for the transport of a dialysate liquid (spent dialysate and liquid ultrafiltered from the blood through a semipermeable membrane 5) from the treatment station 15 towards an evacuation zone, schematically denoted by 16 in FIG. 1.

The hydraulic circuit cooperates with a blood circuit 17, also schematically represented in FIG. 1 in its basic component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 17 of FIG. 1 comprises a blood withdrawal line 6 designed to remove blood from a vascular access 18 and a blood return line 7 designed to return the treated blood to the vascular access 18.

The blood circuit 17 of FIG. 1 further comprises a primary chamber 3, or blood chamber, of the blood filtration unit 2, the secondary chamber 4 of which is connected to the hydraulic circuit 100.

In greater detail, the blood withdrawal line 6 is connected at the inlet of the primary chamber 3, while the blood return line 7 is connected at the outlet of the primary chamber 3.

In turn, the dialysis supply line 8 is connected at the inlet of the secondary chamber 4, while the dialysis effluent line 13 is connected at the outlet of the secondary chamber 4.

The filtration unit 2, for example a dialyzer or a plasma filter or a hemofilter or a hemodiafilter, comprises, as mentioned, the two chambers 3 and 4 which are separated by a semipermeable membrane 5, for example of the hollow-fiber type or plate type.

The blood circuit 17 may also comprise one or more air separators 19: in the example of FIG. 1 a separator 19 is included at the blood return line 7, upstream of a safety valve 20.

Of course other air separators may be present in the blood circuit, such as positioned along the blood withdrawal line 6.

The safety valve 20 may be activated to close the blood return line 7 when, for example, for security reasons the blood return to the vascular access 18 has to be halted.

The extracorporeal blood treatment apparatus 1 may also comprise one or more blood pumps 21, for example positive displacement pumps such as peristaltic pumps; in the example of FIG. 1, a blood pump 21 is included on the blood withdrawal line 6.

The apparatus of above-described embodiment may also comprise a user interface 22 (e.g. a graphic user interface or GUI) and a control unit 12, i.e. a programmed/programmable control unit, connected to the user interface.

The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing device operating, for example, in the blood circuit 17 and/or in the dialysis fluid circuit 32 and commandable between one first operating condition, in which the closing device allows a liquid to flow towards the filtration unit 2, and a second operative position, in which the closing device blocks the passage of liquid towards the filtration unit 2.

In this case, the control unit 12 may be connected to the closing device and programmed to drive the closing device to pass from the first to the second operative condition, should an alarm condition have been detected.

In FIG. 1 the closing device includes the safety valve 20 (e.g. a solenoid valve) controlled by the unit 12 as described above.

Obviously a valve of another nature, either an occlusive pump or a further member configured to selectively prevent and enable fluid passage may be used.

Alternatively or additionally to the safety valve 20, the closing device may also comprise a bypass line 23 which connects the dialysis fluid supply line 8 and the dialysis effluent line 13 bypassing the filtration unit 2, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1.

The check members 24 on command of the control unit close the fluid passage towards the treatment zone and connect the source 14 directly with the dialysis effluent line 13 through the bypass line 23.

Again with the aim of controlling the fluid passage towards the filtration unit 2, a dialysis fluid pump 25 and a dialysate pump 26 may be included, located respectively on the dialysis fluid supply line 8 and on the dialysis effluent line 13 and also operatively connected to the control unit 12.

The apparatus also comprises a dialysis fluid preparation device 9 which may be of any known type, for example including one or more concentrate sources 27, 28 and respective concentrate pumps 29, 30 for the delivery, as well as at least a conductivity sensor 35.

Of course other kinds of dialysis fluid preparation devices 9 might be equivalently used, having a single or further concentrate sources and/or a single or more pumps.

Since the dialysis apparatus may comprise various liquid sources 14 (for example one or more water sources, one or more concentrate sources 27, 28, one or more sources 33 of disinfectant liquids) connected to the dialysis supply line 8 with respective delivery lines 36, 37 and 38, the apparatus may exhibit, at each delivery line, a respective check member (not all are shown) and, for example, comprising a valve member 31 and 34 and/or an occlusive pump.

The preparation device 9 may be any known system configured for on-line preparing dialysis fluid from water and concentrates.

The dialysis supply line 8 fluidly connects the preparation device 9 for preparing dialysis fluid to the filtration unit 2. The preparation device 9 may be, for example, the one described in the U.S. Pat. No. 6,123,847 the content of which is herein incorporated by reference.

As shown, the dialysis supply line 8 connects the preparation device 9 for preparing dialysis fluid to the filtration unit 2 and comprises a main line 40 whose upstream end is intended to be connected to a source 14 of running water.

Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride and/or bicarbonate.

Concentrate pump/s 29, 30 is/are arranged in the delivery line/s 36/37 in order to allow the metered mixing of water and concentrated solution in the main line 40. The concentrate pump/s 29, 30 is/are driven on the basis of the comparison between 1) a target conductivity value for the mixture of liquids formed where the main line 40 joins the delivery line/s 36/37, and 2) the value of the conductivity of this mixture measured by means of a conductivity sensor 35 arranged in the main line 40 immediately downstream of the junction between the main line 40 and the delivery line/s 36/37.

Therefore, as mentioned, the dialysis fluid may contain, for example, ions of sodium, calcium, magnesium and potassium and the preparation device 9 may be configured to prepare the dialysis fluid on the basis of a comparison between a target conductivity value and an actual conductivity value of the dialysis fluid measured by the conductivity sensor 35 of the device 9.

The preparation device 9 comprises regulating means 10, of a known type (i.e. concentrate pump/s 29, 30), which is configured to regulate the concentration of a specific substance, in particular an ionic substance, in the dialysis liquid. Generally it is advantageous to control the sodium concentration of the dialysis fluid.

The dialysis supply line 8 forms an extension of the main line 40 of the preparation device 9 for preparing dialysis fluid. Arranged in this dialysis supply line, in the direction in which the liquid circulates, there are the first flow meter 41 and the dialysis fluid pump 25.

The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value of the dialysate in the dialysis effluent line 13.

In detail, the parameter of the dialysate, which is measured by the sensor 11 is at least one chosen in the group consisting of conductivity of the dialysate, a conductivity-related parameter of the dialysate, concentration of at least a substance in the dialysate and a concentration-related parameter of at least a substance in the dialysate.

In detail the sensor 11 is a conductivity sensor, which is connected to the dialysis effluent line 13, and is configured to detect conductivity values of the dialysate downstream of the filtration unit 2.

Alternatively (or in combination) sensor 11 may include a concentration sensor configured for measuring the concentration of at least one substance in the dialysate, such as sodium concentration.

Correspondingly, sensor 35 on the dialysis fluid supply line may be not a conductivity sensor and, differently, may include a concentration sensor configured for measuring the concentration of at least one substance in the dialysis fluid, such as sodium concentration.

The control unit 12 of the dialysis apparatus represented in FIG. 1 may be connected to a (graphic) user interface 22 through which it may receive instructions, for example target values, such as blood flow rate $Q_b$, dialysis fluid flow rate $Q_{di}$, infusion liquid flow rate $Q_{inf}$ (where appropriate), patient weight loss WL. The control unit 12 furthermore may receive detected values by the sensors of the apparatus, such as the aforementioned flow meters 41, 42, the (e.g. conductivity) sensor 35 of the preparation device 9 and the (e.g. conductivity) sensor 11 in the dialysis effluent line 13. On the basis of the instructions received and the operating modes and algorithms which have been programmed, the control unit 12 drives the actuators of the apparatus, such as the blood pump 21, the aforementioned dialysis fluid and dialysate pumps 25, 26, and the preparation device 9.

As already mentioned, the described embodiments are intended to be non-limiting examples. In particular the circuits of FIG. 1 should not be interpreted as defining or limiting, as an apparatus such as in the invention may comprise other additional or alternative components to those described.

For example an ultrafiltration line may be included, with at least one respective pump connected to the dialysis effluent line 13.

One or more infusion lines 39 may also be included, with respective infusion pumps 43 or flow regulation valves, the infusion lines being connected up to the blood return line 7 and/or the blood withdrawal line 6 and/or directly to the patient. The liquid sources for the infusion lines may be pre-packaged bags 44 and/or liquids prepared by the apparatus itself.

In the example of FIG. 1, an infusion line 39 is shown directly connected to the blood return line 7, in particular to the air separator 19. The infusion line 39 may either receive infusion liquid from a pre-packaged bag 44 (solid line 45a) or from an online preparation trough branch 45b (dotted line).

Of course a pre-infusion line may be alternatively or additionally provided receiving the infusion liquid from a bag or from an online preparation device.

The blood circuit of FIG. 1 is intended for double needle treatments; however, this is a non-limiting example of the blood set.

Indeed, the apparatus may be configured to perform single needle treatments, i.e. the patient is connected to the extracorporeal blood circuit by way of a single needle and the extracorporeal line from the patient is then split into a withdrawal line and a return line, using, for example, an 'Y' connector. During single needle treatment, a blood withdrawal phase removing blood from patient is alternated to a blood return phase in which blood is restituted to the patient.

Furthermore one or more devices for measuring specific substance concentrations might be implemented either (or both) in the dialysis fluid side or (and) in the blood side of the hydraulic circuit. Concentration of calcium, potassium, magnesium, bicarbonate, and/or sodium might be desired to be known.

Finally, the above-cited one or more pumps and all the other necessary temperature, pressure and concentration sensors may operate either on the dialysis supply line 8 and/or on the dialysis effluent line 13, in order to adequately monitor the preparation and movement of the liquid in the hydraulic circuit.

Given the above description of a possible embodiment of extracorporeal blood treatment apparatus, thereafter the specific working of the apparatus and the algorithm programming the control unit are described.

Definitions

We define the "dialysis fluid" as the fluid prepared and introduced to the second chamber (4) of the filtration unit (2), the dialyzer. The dialysis fluid may also be denoted "fresh dialysis fluid".

We define the "dialysate" as the fluid from the outlet from the second chamber (4) of the filtration unit (2), the dialyzer. Dialysate is the spent dialysis fluid, comprising the uremic toxins removed from the blood.

We define 'isonatremic dialysis' as a treatment where the sodium concentration of the dialysis fluid does not change pre- to post-filtration unit 2.

We define 'isotonic dialysis', as a dialysis where the tonicity of the dialysis fluid does not change pre- to post-filtration unit 2.

We define an 'isonatrikalemic dialysis', as a treatment where the sum of sodium and potassium concentrations of the dialysis fluid does not change pre- to post-filtration unit 2.

We define 'isoconductive dialysis', as a dialysis treatment where the conductivity of the dialysis fluid does not change pre- to post-filtration unit 2, $\kappa_{di}=\kappa_{do}$.

We define 'plasma conductivity' (PC, $\kappa_p$) as the conductivity of the dialysis fluid in an isoconductive dialysis.

We define the (plasma) refilling index RI as the ratio between the change of total body water of an individual and a change of her or his hematic volume.

The (plasma) refilling index provides useful indications in understanding the response of a patient subjected to dialysis, in particular her or his behavior concerning vascular "refilling", i.e. the quantity of liquid which is displaced from the interstitial space of the patient's body to the intravascular space thereof.

A possible definition of the refilling index is the following:

$$RI = \frac{\Delta BV\ \%}{WL\ \%}$$

or, alternatively, $$RI = \frac{WL\ \%}{\Delta BV\ \%}$$

where $\Delta BV\ \%$ is the variation in relative hematic volume, i.e. the variation of hematic volume in relation to the total hematic volume, and $WL\ \%$ is the relative weight loss, i.e. the weight loss in relation to the individual's effective weight W.

Though percentage values are used, it is clear that the refilling index may also be defined by the ratio between the hematic volume variation $\Delta BV$ and the weight variation WL.

In this application, when "isotonic treatment" word is used alone, this actually implies isotonic, isonatremic or isonatrikalemic dialyses.

Glossary

The following terms are consistently used throughout the equations provided in the following description of the detailed working of the extracorporeal blood treatment apparatus.

| Name | Description | Unit |
|---|---|---|
| $\kappa_{d,pre}=\kappa_{di}$ | Dialysis fluid conductivity upstream the filtration unit (corresponding to final conductivity of the dialysis fluid); | mS/cm |
| $\kappa_{d,post}=\kappa_{do}$ | Dialysate conductivity downstream the filtration unit; | mS/cm |
| $PC=\kappa_p$ | Plasma conductivity; | mS/cm |
| $Q_{di}$ | Dialysis fluid flow rate at filtration unit inlet; | mL/min |
| $Q_{uf}$ | Ultrafiltration flow rate; | mL/min |
| $Q_{do}$ | Dialysate flow rate at filtration unit outlet (i.e., $Q_{di}+Q_{uf}$); | mL/min |
| $Q_{b,set}$ | Set blood flow rate or set blood water flow rate at filtration unit inlet; | mL/min |
| $Q_b$ | Real blood flow rate at filtration unit inlet (set blood flow compensated for arterial pressure); | mL/min |
| $Q_{bw}$ | Real blood water flow rate at filtration unit inlet; | mL/min |
| $K_u$ | Filtration unit clearance for urea; | mL/min |
| KoA | Urea mass transfer area coefficient of filtration unit (average of normally used dialyzers); | mL/min |
| $C_{di,Na,start}$ | Dialysis fluid concentration of sodium ions (Na$^+$) at the start of treatment, automatically calculated and set by the machine before the start of the treatment; | mmol/L |
| $C_{di,Na,\kappa p,pre}$ | Dialysis fluid concentration of sodium ions (Na$^+$) at isoconductive dialysis, i.e., when the dialysis fluid conductivity $\kappa_{di}$ matches the estimated pre-dialysis plasma conductivity $\kappa_{p,pre}$; | mmol/L |
| $C_{di,Na,set,isotonic}$ | Dialysis fluid concentration of sodium ions (Na$^+$) to provide isotonic dialysis; | mmol/L |
| $C_{di,Na,isotonic,adj}$ | Sodium set point adjustment (relative to isoconductive state) required to provide isotonic dialysis; | mmol/L |
| $C_{di,Na,set,isoNa}$ | Dialysis fluid concentration of sodium to provide isonatremic dialysis; | mmol/L |
| $C_{di,Na,isoNa,adj}$ | Sodium set point adjustment (relative to isoconductive state) required to provide isonatremic dialysis; | mmol/L |
| $C_{di,Na,set,isoNa+K}$ | Dialysis fluid concentration of sodium to provide isonatrikalemic dialysis; | mmol/L |
| $C_{di,Na,isoNa+K,adj}$ | Sodium set point adjustment (relative to isoconductive state) required to provide isonatrikalemic dialysis; | mmol/L |
| $C_{di,HCO3}$ | Dialysis fluid concentration of bicarbonate as set by the operator; | mmol/L |
| $C_{di,K}$ | Dialysis fluid concentration of potassium ions (K$^+$) as determined by the used concentrate; | mmol/L |
| $C_{di,Ac}$ | Dialysis fluid concentration of acetate as determined by the used concentrate; | mmol/L |
| $C_{di,g}$ | Dialysis fluid concentration of glucose as determined by the used concentrate; | mmol/L |
| $C_{pw,Na}$ | Estimated or measured pre-dialysis concentration of sodium ions (Na$^+$) in plasma water | mmol/L |
| $C_{pw,HCO3}$ | Estimated or measured pre-dialysis concentration of bicarbonate anions (HCO$_3^-$) in plasma water | mmol/L |
| $C_{pw,Ac}$ | Estimated or measured pre-dialysis concentration of acetate anions (CH3COO$^-$) in plasma water | mmol/L |
| $C_{pw,K}$ | Estimated or measured pre-dialysis concentration of potassium ions (K$^+$) in plasma water | mmol/L |
| $C_{p,g}$ | Estimated or measured pre-dialysis concentration of glucose in plasma | mmol/L |
| $C_{p,u}$ | Estimated or measured pre-dialysis concentration of urea in plasma | mmol/L |
| $f_{bw}$ | Apparent blood water fraction, i.e., the part of whole blood that appears as pure water for urea; | Dimensionless |
| $f_{pw}$ | Plasma water fraction, i.e., the part of plasma that is pure water; | Dimensionless |
| $f_{g,KB}$ | Glucose clearance fraction, i.e., the relative glucose clearance compared to urea clearance; | Dimensionless |
| $\kappa_{0,di}$ | Dialysis fluid conductivity at filtration unit inlet for a pure electrolyte solution (i.e. without glucose, either because the actual solution does not contain glucose, or because the conductivity has been compensated for the influence of glucose); | mS/cm |
| $\kappa_{0,do}$ | Dialysate conductivity at filtration unit outlet for a pure electrolyte solution (i.e. without glucose and urea, because the conductivity has been compensated for the influence of glucose and urea); | mS/cm |

-continued

| Name | Description | Unit |
|---|---|---|
| $\kappa_{p,1}$ and $\kappa_{p,2}$ | 1st and 2nd estimate of plasma conductivity; | mS/cm |
| $\kappa_{p,pre}$ | Estimate of plasma conductivity at beginning of treatment (representing a pre-dialysis value); | mS/cm |
| $\kappa_{isotonic}$ | Conductivity offset between $\kappa_{do}$ and $\kappa_{di}$ to provide isotonic dialysis (correspondent to $c_{di,Na,isotonic,adj}$); | mS/cm |
| $\kappa_{isoNa}$ | Conductivity offset between $\kappa_{do}$ and $\kappa_{di}$ to provide isonatremic dialysis (correspondent to $c_{di,Na,isoNa,adj}$); | mS/cm |
| $\kappa_{isoNa+K}$ | Conductivity offset between $\kappa_{do}$ and $\kappa_{di}$ to provide isonatrikalemic dialysis (correspondent to $c_{di,Na,isoNa+K,adj}$); | mS/cm |
| $\kappa_{rest1}$ | Conductivity contribution from lesser solutes 1; | mS/cm |
| $\kappa_{rest2}$ | Conductivity contribution from lesser solutes 2; | mS/cm |
| $\kappa_{rest3}$ | Conductivity contribution from lesser solutes 3; | mS/cm |
| $\gamma_g$ | Conductivity correction term for glucose; | M − 1 = L/mol |
| $\gamma_u$ | Conductivity correction term for urea; | M − 1 = L/mol |
| $M_{\kappa_{NaHCO_3}}$ | Molar conductivity of sodium bicarbonate (NaHCO$_3$) at ionic strength 150 mM; | L · mS/ mol · cm |
| $M_{\kappa_{NaCl}}$ | Molar conductivity of sodium chloride (NaCl) at ionic strength 150 mM; | L · mS/ mol · cm |
| $M_{\kappa_{NaAc}}$ | Molar conductivity of sodium acetate (NaCH$_3$COO) at ionic strength 150 mM; | L · mS/ mol · cm |
| $M_{\kappa_{KCl}}$ | Molar conductivity of potassium chloride (KCl) at ionic strength 150 mM; | L · mS/ mol · cm |
| T | Set total treatment time; | min |
| t | Elapsed time into treatment; | min |
| α | Donnan factor; | Dimensionless |
| Cond$_{prop}$ | Proposed value for conductivity in the dialysis fluid; | mS/cm |
| Cond$_{set}$ | Set value for conductivity in the dialysis fluid; | mS/cm |
| W | Patient weight | Kg |
| UF volume | Ultrafiltration volume | L |
| WL | Weight loss | Kg |
| $g_{conc}$ | Glucose concentration | g/L |
| $\beta_1$ | Conversion coefficient for conductivity when referred to WL/W | mS/cm |
| | Conversion coefficient for concentration when referred to WL/W | mmol/ L |
| $\beta_2$ | Conversion coefficient for conductivity | $\dfrac{mS/cm}{g/L}$ |
| | Conversion coefficient for concentration | mmol/g |

The Donnan factor indicates a value of electroneutrality to be kept over the membrane. For estimating the Donnan factor reference is made to Trans Am Soc Artif Intern Organs, 1983; 29; 684-7, "Sodium Fluxes during hemodialysis", Lauer A., Belledonne M., Saccaggi A., Glabman S., Bosch J.

Solution Proposal

The technical solution here described consists of three main parts:
  Estimating PC at the beginning of the treatment (i.e., $\kappa_{p,pre}$);
  Determining the dialysis fluid sodium concentration such that, if applied, the dialysis fluid tonicity (or sodium or sodium+potassium) is substantially not changed during its passage through the filtration unit;
  Setting dialysis fluid sodium concentration applying an additional offset according to a specific function particularly to take into account of high deviations from an average pre-dialysis plasma sodium concentration;
  Maintaining the dialysis fluid composition throughout the whole treatment.

The various steps of the proposed method described below are intended to be performed by the control unit 12 of the extracorporeal blood treatment device 1, even if not explicitly stated.

In particular a treatment session is started, preferably, but not necessarily, as a double needle hemodialysis treatment.

The user shall input the prescription values through the user interface 22. For example the set values for total weight loss WL and total treatment time T are provided, as well as the blood flow rate $Q_b$ and the fresh dialysis flow rate $Q_{di}$.

Other parameters may be entered through the user interface, such as bag type, sodium user limits, etc.

The operator has to further input the 'bicarbonate' set before starting the treatment.

The control unit 12 calculates either the initial dialysis liquid conductivity or the initial concentration of at least one solute, e.g. sodium, in the dialysis liquid in order to start with a dialysis fluid conductivity as close as possible to the expected patient pre-dialytic plasma conductivity.

In order to not disturb the tonicity of the patient, it is necessary to set the fluid composition as quickly as possible so that the patient initial plasma conductivity is not inadvertently changed. Thus, estimating of the plasma conductivity has to be done as rapidly as possible when treatment starts; moreover, since the estimation is preferably performed only once, this measure should be as reliable as possible.

In this respect it is worth to note that, in the following detailed description, reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

Given the above, the control unit 12 sets a first parameter value for the dialysis fluid in the dialysis fluid supply line 8 at an initial set point; in general the first parameter of the dialysis fluid is either the conductivity of the dialysis fluid, or a conductivity-related parameter of the dialysis fluid, or concentration of at least a substance (in particular an ionic substance and in more detail sodium) in the dialysis fluid, or a concentration-related parameter of at least a substance (e.g. sodium) in the dialysis fluid.

In detail, the control unit 12 is configured to set the first parameter value for the dialysis fluid at the initial set point so that a dialysis fluid conductivity matches a first estimate of the plasma conductivity of the blood.

In the specific, the control unit 12 calculates the initial set point of the substance concentration and drives the regulating means 10 acting on the sodium concentration in the dialysis liquid.

The set point is calculated before starting the blood circulation (i.e. before starting the treatment).

In order to calculate the dialysis composition initial set point alternative ways might be used, e.g. determine a certain sodium concentration (see below), or using an average plasma conductivity from a large population, or using an average plasma conductivity from a large population corrected for the composition of the dialysis fluid, or calculate based on historic patient data.

In any case, the initial set point for the dialysis liquid is calculated by the control unit 12 so that the expected plasma conductivity is the best guess of plasma conductivity that may be calculated, without prior knowledge of the individual patient.

In general terms, the control unit is configured to calculate the initial set point of the substance concentration to be set (e.g. sodium) in the dialysis fluid as a function of the difference in concentration of at least one (and in detail several) further substance in the dialysis fluid and the same further substance in the plasma.

Specifically, the control unit 12 is configured to calculate the initial set point of sodium concentration to be set in the dialysis fluid before the start of the treatment using the following relationship:

$$c_{di,Na,start} = \alpha * c_{pw,Na} + \frac{1}{M_{\kappa_{NaCl}}}(M_{\kappa_{NaHCO_3}} - M_{\kappa_{NaCl}})\left(\frac{1}{\alpha} * c_{pw,HCO_3} - C_{di,HCO_3}\right) + + \frac{1}{M_{\kappa_{NaCl}}}(M_{\kappa_{NaAc}} - M_{\kappa_{NaCl}})\left(\frac{1}{\alpha} * c_{pw,Ac} - C_{di,Ac}\right) + \frac{M_{\kappa_{KCl}}}{M_{\kappa_{NaCl}}}(\alpha * c_{pw,K} - c_{di,k}) + + \frac{1}{M_{\kappa_{NaCl}}}\frac{Q_{do}}{K_u}(\kappa_{rest3}) \quad (1)$$

wherein the used symbols meaning is clarified in the glossary section.

Since $K_u$ may not be known at dialysis start, a fixed value equal to $Q_{di}/2$ may be possibly used or calculated with a formula taking the filtration unit characteristics to be a mean value for the used type of filtration unit or the value for the actual filtration unit.

Of course, different mathematical relationships may be used taking into account exclusively some of the considered substances and/or exclusively some of the conductivities and/or molar differences.

Once the sodium initial set point has been calculated and a corresponding dialysis fluid has been prepared by the control unit 12 driving the regulating means 10, the treatment may start.

The dialysis fluid is circulated through the dialysis fluid circuit 32 and the secondary chamber 4 of the filtration unit 2 so as to exchange with blood.

Correspondingly, blood is withdrawn from the patient and circulated in the extracorporeal blood circuit 17 and particularly is circulated through the primary chamber 3 of the filtration unit 2.

At least one, and in general a plurality, of consecutive initial values of the parameter (in the specific example, the conductivity) of the dialysate downstream of the secondary chamber 4 are measured at the beginning of the treatment through sensor 11.

The control unit 12 is configured to validate and further process the measurement of an initial value of the conductivity of the dialysate as soon as the diffusion process in the filtration unit 2 reaches stable conditions.

Indeed, a transient exists when dialysis fluid and blood start exchanging during which the dialyzer outlet conductivity is not stable; during the transient period the measured outlet conductivity values should be disregarded.

The stability condition may be determined by observing, on a 1-minute window, the first derivative of $\kappa_{do}$ and checking when it is lower in size than a fixed threshold. Once this stability criterion is fulfilled, $\kappa_{do}$ is taken as the median value on the 1-minute window. The first derivative is used to avoid the presence of possible drifts in the outlet conductivity. Extracting the median and/or the average value of $\kappa_{do}$ allows discharging possible outliers of the outlet conductivity signal from the average calculation.

In order to minimize the time needed to reach stability conditions, changes in dialysis fluid flow rate and in bicarbonate prescription may be prevented during this preliminary isotonic sodium identification phase.

The control unit 12 may compensate the measured initial conductivity value of the dialysate as a function of the concentration of glucose and/or urea. Alternatively, account of glucose and urea may be taken once the plasma conductivity is determined and an adjustment factor calculated as explained in the following description.

Correction based on main electrically neutral substances is optional and may be used or not to increase accuracy.

It is worth to note that the initial conductivity of the fresh dialysis fluid upstream the secondary chamber 4 may be either measured or taken as the set value for dialysis conductivity.

In general, it is preferred to measure the initial conductivity of the dialysis fluid through the sensor 35, too.

It is important to underline that the initial setting of the sodium concentration calculated or determined as above stated to be as close as possible to the expected plasma conductivity (eq. 1) may be optional, meaning that the method for estimating the initial plasma conductivity may be performed even if the sodium content of the dialysis conductivity is initially simply set by the operator.

Vice versa, it may be relevant to measure at least the conductivity downstream the filtration unit (and preferably also the conductivity upstream the filtration unit) as soon as possible, i.e. as soon as stable conditions are reached or as soon as an estimate of such conductivity in stable conditions may be performed.

This is due to the need of matching as much as possible the patient initial plasma conductivity which is clearly affected/changed by the different conductivity of the dialysis fluid circulating during the treatment.

In order to make a first estimate of the plasma conductivity based on measured values, two embodiments are provided, which may be used together or alternatively.

Firstly, the control unit 12 calculates the value of the initial plasma conductivity, based on the measured initial parameter value of the dialysate (i.e. based on conductivity or concentration measurement of dialysate on the filtration unit outlet) and on the corresponding parameter value of the dialysis fluid in the dialysis fluid supply line 8 e.g. conductivity or concentration). During the start of the treatment and particularly during circulating the dialysis fluid through the secondary chamber 4 up to measuring the initial value of the parameter of the dialysate downstream of the secondary chamber used for the calculating of the initial plasma conductivity, the dialysis fluid conductivity (or concentration) is kept substantially constant.

Just a single reliable measurement at the inlet and at the outlet of the dialyzer may be sufficient to have a preliminary (to be made more accurate) or an already final estimation of the PC. From a general point of view, the control unit 12 is further configured to calculate the plasma conductivity as a function of at least one or more flow rates. The flow rates include the dialysate flow rate at the outlet of the secondary chamber 4; in addition, the flow rates may include the blood flow rate in the blood lines too.

Specifically, according to the first embodiment, the control unit 12 is configured to calculate the plasma conductivity using the following formula:

$$\kappa'_{p,1} = \kappa_{0,do} + \frac{Q_{do}}{Q_{Bset}}(\kappa_{0,do} - \kappa_{0,di}) \quad (2)$$

The significance of the denotations above is given in the Glossary.

According to the second embodiment, the control unit 12 is configured to calculate the plasma conductivity using the following formula:

$$\kappa''_{p,1} = \kappa_{0,di} + \frac{Q_{do}}{K_u}(\kappa_{0,do} - \kappa_{0,di}) \quad (3)$$

The significance of the denotations and constants above is given in the Glossary.

It is worth to underline that during the above described calculation of the initial plasma conductivity (formulas (2) and (3)), the dialysis fluid circulates through the secondary chamber 4 maintaining the dialysis fluid parameter value substantially constant.

According to first estimate, $k_{p,1}$ may be found after approx. 6 to 10 minutes after treatment start.

Of course, both formulas (2) and (3) for estimation of plasma conductivity may be iteratively applied, meaning that the newly calculated estimate of PC ($k_{p,1}$) is imposed to the dialysis fluid and a new estimate again calculated after taking measures of the conductivity at the inlet and outlet of the filter as soon as stable conditions are reached.

Of course, in case of iteration of anyone of the above calculations according to formulas (2) or (3), after the first plasma conductivity estimation, the dialysis fluid parameter value is changed since the newly calculated estimate of PC ($k_{p,1}$) is imposed to the dialysis fluid, meaning that the conductivity of the dialysis fluid is changed. This however does not impact on the fact that the first calculation according to formulas (2) and (3) is made without a change in the conductivity of the dialysis fluid.

The dialysis fluid sodium concentration correspondent to $k_{p,pre}$ is then determined.

The resulting dialysis fluid sodium concentration applied, $c_{di,Na,kp,pre}$, would correspond to implement an isoconductive dialysis.

However, since an isotonic or isonatremic or isonatrikalemic dialysis is to be in principle applied, this sodium value may be adjusted with a proper adjustment factor (depending on the choice to apply isotonic, isonatremic or isonatrikalemic dialysis).

In respect to the above mentioned treatments, it is relevant to note the following.

An isonatremic dialysis may in general terms be considered as a treatment where the sodium concentration in the extracellular fluid of the patient is maintained stable or undergoes reduced variations throughout treatment.

It is however worth noting that tonicity is determined by the particles that are osmotically active.

Actually, the dialysis fluid (and the plasma) contains a multitude of substances that influence tonicity/osmolality, not just sodium, even if this is the main determinant of serum osmolality.

Hence, an isotonic dialysis may be considered as a dialysis where the tonicity of the fluids in the patient is maintained stable throughout treatment or undergoes reduced variations throughout treatment. This would be achieved by maintaining the tonicity of the dialysis fluid substantially equal to the tonicity of the extracellular fluid throughout treatment. In this case, the tonicity of the dialysis fluid does not change pre- to post-filtration unit 2.

An isonatrikalemic dialysis, may in general terms be considered as a treatment where the sum of sodium and potassium concentrations in the patient extracellular fluid is maintained stable or undergoes reduced variations throughout treatment (in this case, the sum of sodium and potassium concentrations of the dialysis fluid does not change pre- to post-filtration unit 2). Considering that a patient shall lose a certain amount of potassium during treatment, the isonatrikalemic condition may be maintained with a proportional increase in serum sodium concentration. In general, a patient has a potassium overload which is to be reduced; at the same time, in an isonatrikalemic dialysis it is desired not to change too much the tonicity of the blood, therefore potassium is reduced, but the sum of sodium and potassium is kept constant (i.e. plasma sodium slightly increases).

An isoconductive dialysis may in general terms be considered as a dialysis treatment maintaining the conductivity of the dialysis fluid equal to the conductivity of the extracellular fluid, which in this case is represented by the plasma conductivity.

The plasma conductivity (PC, $\kappa_p$) is the conductivity at which the dialysis fluid conductivity is not changed during its passage through the dialyzer. Then the conductivities upstream and downstream the filtration unit 2 are equal: $\kappa_{di} = \kappa_{do}$. In case of an isotonic or isonatremic or isonatrikalemic treatment is to be performed, the mentioned adjustment factor is calculated based on molar conductivities, dialysis fluid composition and the best estimate of plasma water composition as will better emerge from the following description. The best estimate of plasma water composition may be derived from literature, or may be based on statistical prepared values, or test of patient, or obtained with direct lab measurements made before the treatment.

According to an aspect, the control unit 12 receives a value representative of a parameter of the blood in said blood lines 6, 7. The blood parameter may be the plasma conductivity or a plasma conductivity-related parameter.

In particular, the control unit 12 may be programmed for calculating the plasma conductivity, for example executing the method previously disclosed or, alternatively using known methods such as those described in EP 2377563.

Alternatively, the control unit 12 directly receives as an input the plasma conductivity. For example, the physician or the nurse may receive a lab analysis and may provide the datum to the machine through the user interface of the dialysis monitor; the control unit 12 is programmed for storing in a memory the plasma conductivity to be used for the following dialysis fluid parameter regulation.

Finally, the plasma conductivity may be directly measured in vivo by the monitor before starting the treatment session using a proper plasma conductivity sensor.

The control unit 12 is generally configured for setting a value of a first parameter for the dialysis fluid in the dialysis supply line 8 at a set point.

The first parameter for the dialysis fluid is chosen between a conductivity of the dialysis fluid, a conductivity-related parameter of the dialysis fluid, a concentration of a substance in the dialysis fluid and a concentration-related parameter of a substance in the dialysis fluid.

Depending on the specific dialysis monitor, the sodium content (or the content of more than one electrolyte) may be regulated in the dialysis line. Alternatively, the control parameter may be the overall conductivity of the dialysis fluid.

The setting of the value of the first parameter in the dialysis fluid (which is hereinafter generally identified as sodium concentration set point in the dialysis fluid with no limiting effect) may include a first and a second adjustment step.

In the first adjustment step, a proposed value for the first parameter is determined (e.g. a proposed sodium concentration value is calculated).

In the second adjustment step, a set value for the first parameter is calculated as a function of the proposed value (e.g. a set value for conductivity in the dialysis fluid is calculated starting from the proposed value).

The first adjustment step includes the sub-step of calculating the sodium concentration set point as a function of a main contribution term based on/function of the plasma conductivity and as a function of an adjustment contribution term, i.e. a term which takes into account the transport driving gradient of certain specific substances.

The calculation is an algebraic sum of at least the main contribution term $C_{di,Na,\kappa_{p,pre}}$ and the adjustment contribution term $C_{di,Na,adj}$ according to the following general formula:

$$C_{di,Na,set} = C_{di,Na,\kappa_{p,pre}} + C_{di,Na,adj}$$

In order to obtain a dialysis fluid sodium implementing a certain kind of dialysis, i.e. $C_{di,Na,set}$, an adjustment factor $C_{di,Na,adj}$ needs to be applied to make the dialysis fluid matching a certain specific concentration of the plasma.

$C_{di,Na,\kappa_{p,pre}}$ is the dialysis fluid concentration of sodium at isoconductive state, i.e. when the dialysis fluid conductivity $\kappa_{di}$ matches the estimated pre-dialysis plasma conductivity $\kappa_{p,pre}$.

Though not essential since a calculation may be made based on conductivities too, the main contribution term and the adjustment contribution term are dimensionally concentrations of a substance (e.g. sodium) in a fluid.

The adjustment contribution term is the sodium concentration set point adjustment relative to an isoconductive state to provide a specific treatment which may be, for example, chosen in the group including isotonic dialysis, isonatremic dialysis and isonatrikalemic dialysis.

The Applicant has understood that certain specific substances, namely bicarbonate, potassium, acetate, and citrate have a major effect which should be taken into account when it is desired to run a purely isotonic, or isonatric, or isonatrikalemic dialysis treatment. Indeed, an isoconductive dialysis (i.e. a dialysis maintaining the conductivity of the dialysis fluid equal to the conductivity of the extracellular fluid, which in this case is represented by the plasma conductivity—as defined, plasma conductivity PC, $\kappa_p$ as the conductivity at which the dialysis fluid conductivity is not changed during its passage through the dialyzer so that the pre-dialyzer and the post-dialyzer conductivities are equal: $\kappa_{di} = \kappa_{do}$) causes an overload of sodium in the patient.

To avoid overloading at least the effect of the above substances must be taken into duly consideration. Of course other substances play a role, such as lactate, magnesium, and calcium.

Furthermore, the difference in concentration between same substances in the blood and in the dialysis fluid influences, as well, the sodium overload in case of isoconductive treatments.

Given the above, the Applicant also realized that in calculating the adjustment contribution term, certain parameters having a weight in determining the overload of sodium are known and depends on the machine dressing (e.g. used concentrates) or on the prescription for the patient (e.g. dialysate flow rate). Other parameters depend on the patient undergoing the treatment and therefore may be either directly measured (e.g. lab analysis) or estimated (e.g. based on large population numbers or patient history).

Since isoconductive dialysis causes sodium overload, the adjustment contribution term generally assumes a negative value, i.e. reduces the set point concentration of sodium in the dialysis fluid calculated for isoconductive treatment.

In order to obtain a dialysis fluid sodium implementing isotonic dialysis, i.e. $c_{di,Na,set,isotonic}$, an adjustment factor $c_{di,Na,isotonic,adj}$ needs to be applied to make the dialysis fluid matching the tonicity of the plasma:

$$c_{di,Na,set,isotonic} = c_{di,Na,\kappa_{p,pre}} + c_{di,Na,isotonic,adj} \quad (4)$$

where:

$$c_{di,Na,isotonic,adj} = \quad (5)$$
$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right) + \right.$$
$$(M_{\kappa_{NaAc}} - M_{\kappa_{NaCl}})\left(\frac{1}{\alpha} * c_{pw,Ac} - c_{di,Ac}\right) + +$$
$$\left.(M_{\kappa_{KCl}} - M_{\kappa_{NaCl}})(\alpha * c_{pw,K} - c_{di,k}) + \frac{Q_{do}}{K_u}(k_{rest1} + k_{rest2})\right)$$

The significance of the denotations and constants above is given in the Glossary.

Factor k (namely, $k_{rest1}$, $k_{rest2}$ and $k_{rest3}$—see also the following formulas (10) and (11)) defines the effect on the conductivity due to other components in the dialysis fluid different from the components already treated and included in the respective formula. Thus, the effect of salts containing calcium, magnesium, lactate, phosphate, and sulphate, but also glucose and urea, may have upon the conductivity. The effect created by these components is most often small, and does not vary considerably between the dialysis treatments.

In order to obtain a dialysis fluid sodium implementing isonatremic dialysis, i.e. $c_{di,Na,set,isoNa}$, an adjustment factor $c_{di,Na,isoNa,adj}$ needs to be applied to make the sodium concentration of dialysate out from the dialyzer matching the sodium concentration of dialysis fluid at the inlet of the dialyzer:

$$c_{di,Na,set,isoNa} = c_{di,Na,\kappa_{p,pre}} + c_{di,Na,isoNa,adj} \quad (6)$$

where:

$$c_{di,Na,isoNa,adj} = \quad (7)$$
$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right) + \right.$$
$$(M_{\kappa_{NaAc}} - M_{\kappa_{NaCl}})\left(\frac{1}{\alpha} * c_{pw,Ac} - c_{di,Ac}\right) + +$$
$$\left.M_{\kappa_{KCl}}(\alpha * c_{pw,K} - c_{di,k}) + \frac{Q_{do}}{K_u}k_{rest3}\right)$$

The significance of the denotations and constants above is given in the Glossary.

In order to obtain a dialysis fluid sodium implementing isonatrikalemic dialysis, i.e. $c_{di,Na,set,isoNa+K}$, an adjustment factor $c_{di,Na,isoNa+K,adj}$ needs to be applied to make the sum of sodium and potassium concentrations of dialysate out from the dialyzer matching the corresponding sum of concentrations of dialysis fluid at the inlet of the dialyzer:

$$c_{di,Na,set,isoNa+K} = c_{di,Na,\kappa_p,pre} + c_{di,Na,isoNa+K,adj} \quad (8)$$

where:

$$c_{di,Na,isoNa+K,adj} = \quad (9)$$
$$-\frac{1}{M_{\kappa_{NaCl}}}\left((M_{\kappa_{NaHCO_3}} - M_{\kappa_{NaCl}})\left(\frac{1}{\alpha}*c_{pw,HCO_3} - c_{di,HCO_3}\right) + \right.$$
$$(M_{\kappa_{NaAc}} - M_{\kappa_{NaCl}})\left(\frac{1}{\alpha}*c_{pw,Ac} - c_{di,Ac}\right) + +$$
$$\left. (M_{\kappa_{KCl}} - M_{\kappa_{NaCl}})(\alpha*c_{pw,K} - c_{di,K}) + \frac{Q_{do}}{K_u}\kappa_{rest3}\right)$$

The significance of the denotations and constants above is given in the Glossary.

Of course, different formulas including one or more of the substances above stated may be alternatively used.

Once the proposed value for sodium concentration in the dialysis fluid is calculated, the control unit 12 may either directly use the calculated proposed value for properly regulating the conductivity or the concentration of the substance in the fresh dialysis fluid or may apply for the second adjustment step.

For a big patient population, the average pre-dialysis plasma sodium concentration is approximately 138 mmol/l. However, patients may have pre-dialysis plasma sodium in the range 130-143 mmol/l (or even lower or higher); moreover, patient plasma sodium vary considerably, both between patients and within a single patient.

In some identified cases, the pre-dialysis value of sodium concentration or plasma conductivity may be artificially low.

This 'low sodium set point'/'low conductivity' may happen if the patient is fluid overloaded. This may also happen in diabetics who come in with high glucose values. If the proposed value for conductivity of the dialysis fluid (or sodium concentration) is used, then the plasma conductivity may be controlled to a too low value.

In these situations, it may be desirable to possibly apply a further adjustment factor or offset to the proposed value $Cond_{prop}$ of the first parameter for the dialysis liquid to take into account of these too low values.

Notably, the proposed value $Cond_{prop}$ of the first parameter is either calculated by the control unit 12, for example in accordance with the previously described steps or is received as an input, e.g. the nurse or the physician may directly input the proposed value into the apparatus receiving said value from a lab measurement or from previous treatment sessions, for example.

Moreover, the proposed value $Cond_{prop}$ of the first parameter may be either a conductivity value for the dialysis fluid or a concentration value for a substance, which might be sodium and/or another ionic substance contained in the dialysis liquid.

In case the first parameter is the concentration of at least a substance in the dialysis fluid (e.g. sodium), the proposed value $Cond_{prop}$ for the first parameter may be the substance concentration set point for running a pure isotonic dialysis or pure isonatremic dialysis or pure isonatrikalemic dialysis. In other terms, the proposed value $Cond_{prop}$ may be coincident with i.e. $c_{di,Na,set,isoNa}$ (dialysis fluid sodium concentration implementing isonatremic dialysis), or $c_{di,Na,set,isoNa+K}$ (dialysis fluid sodium concentration implementing isonatrikalemic dialysis), or $c_{di,Na,set,isotonic}$ (dialysis fluid sodium concentration implementing isotonic dialysis).

Alternatively, the proposed value $Cond_{prop}$ for the first parameter may be the substance concentration set point for running an isoconductive dialysis, i.e. $C_{di,Na,\kappa_{p,pre}}$. In this case, the substance concentration set point for running an isoconductive dialysis may be calculated according to the method disclosed in the previous description or calculated according to the method described, for example, in EP 547025 or in EP 920877.

Vice versa, in case the first parameter is the dialysis fluid conductivity (as per the following non-limiting description), the proposed value $Cond_{prop}$ for the first parameter is correspondingly the conductivity set point for running an isotonic dialysis or isonatremic dialysis or an isonatrikalemic dialysis or an isoconductive dialysis, as the case may be.

Once the proposed value $Cond_{prop}$ for the first parameter is obtained (i.e. calculated or received), the control unit 12 determines a set value $Cond_{set}$ for the first parameter as a function of the proposed value $Cond_{prop}$ for the first parameter.

The basic idea is to modify the dialysis fluid set point (either by controlling conductivity or a substance—e.g. sodium—concentration), so that in general it is not directly equal to the estimated plasma conductivity for an isoconductive treatment or modified (e.g. adjusted as above described) conductivity for an isotonic, or isonatremic, or isonatrikalemic treatment.

The control unit 12 obtains (i.e. receives as an input or calculates) a value for a second and/or a third parameter and determines a set value $Cond_{set}$ for the first parameter as a function of the proposed value $Cond_{prop}$ for the first parameter and at least one of the second and third parameter.

The second parameter is related to, in general indicative of, a patient fluid overload. Indeed, in such patients, the sodium concentration or plasma conductivity might be artificially low.

According to some embodiments, it is proposed to correct the proposed value $Cond_{prop}$ for the first parameter based on the second parameter, i.e. based on the patient fluid overload.

As to the specific second parameter to be used, a first approach is to consider the weight loss WL set for the patient. The higher it is the weight loss WL, the higher should be the patient fluid overload and consequently the corrective action.

In case of hemodialysis (i.e. no substitution fluid infusions), the weight loss may be substituted with the ultrafiltration volume (UF volume).

Of course, also the weight loss rate WLR or the ultrafiltration rate UFR may be suitable parameter, at least partly reflecting the patient fluid overload.

An even more reliable choice for the second parameter is the ratio between the weight loss WL (or WLR or UF volume or UFR) and a patient weight W, e.g.:

$$\frac{WL}{W}$$

Indeed, the same weight loss WL (or WLR or UF volume or UFR) applied to a high weight patient or to a low weight patient reflects different situations: in the second case, the patient is much more fluid overloaded than in the first mentioned case.

In this formula, different weights W for the patient may be used, for example this value can be the weight of the patient before treatment (known as the wet weight) or the patient's weight after the treatment (known as the dry weight), or it can be the weight of the patient's bodily water (before or after the treatment). The weight of the bodily water is calculable, as is known, as a function of the total weight of the patient, for example via a proportionality factor (sometimes known as the bodily weight distribution volume) which is normally considered to be between 50% and 60%, for example 55%.

In further embodiments, the second parameter may be a difference between an overloaded weight (e.g. wet weight or bodily water before the treatment) of the patient and a non-overloaded weight for the patient (e.g. dry weight or bodily water after the treatment).

Other possible choices for the second parameter are the refilling index (RI) or even the absolute blood volume of the patient.

A first exemplificative approach consists in determining the set value $Cond_{set}$ for the first parameter as a linear function of this second parameter.

In the following reference is made to the second parameter being the ratio between the weight loss (WL) and the patient weight (W). Also the ratio between the ultrafiltration volume (UF volume) and the patient weight (W) is a recommended second parameter.

However, any of the previously mentioned choices for the second parameter might be alternatively, or in combination, used, with a corresponding change in parameter value.

The control unit 12 may be configured to determine the set value ($Cond_{set}$) for the first parameter as a weighted function of the second parameter:

$$Cond_{set} = \beta_1 \cdot \frac{WL}{W} + \text{offset} \qquad (10)$$

optionally $\beta_1$ is a constant.

In more detail, the control unit 12 may be configured to determine the set value $Cond_{set}$ for the first parameter according to the following mathematical relationship:

$$Cond_{set} = Cond_{prop} + \beta_1 \cdot \frac{WL}{W} + \text{offset} \qquad (11)$$

wherein $Cond_{prop}$ is the proposed value for the first parameter for the dialysis fluid in the dialysis supply line 8. The offset may be or may be not present.

For example, in case the first parameter is conductivity and the second parameter is the weight loss (WL), a correct value for $\beta_1$ is included between 0 and 0.3: $0<\beta_1<0.3$; in particular included in the range between 0 to 0.15: $0<\beta_1\leq 0.15$ ($\beta_1$ unit being mS/cm/kg).

In case the first parameter is conductivity and the second parameter is the relative weight loss (WL/W), a correct value for $\beta_1$ is included between 0 and 25: $0<\beta_1<25$; in particular included in the range between 0 to 12.5: $0<\beta_1\leq 12.5$ ($\beta_1$ unit being mS/cm).

Vice versa, in case the first parameter is concentration and the second parameter is the weight loss (WL), a correct value for $\beta_1$ is included between 0 and 3: $0<\beta_1<3$; in particular included in the range between 0 to 1.5: $0<\beta_1\leq 1.5$ ($\beta_1$ unit being mmol/L/kg).

In case the first parameter is concentration and the second parameter is the relative weight loss (WL/W), a correct value for $\beta_1$ is included between 0 and 250: $0<\beta_1<250$; in particular included in the range between 0 to 125: $0<\beta_1\leq 125$ ($\beta_1$ unit being mmol/L).

Of course, in case another second parameter is selected, a different absolute value/range of values and different units of measure are used.

In general, the control unit 12 is configured to determine the set value $Cond_{set}$ for the first parameter as an algebraic sum of at least a first term and a second term: the first term is function of the proposed value $Cond_{prop}$ (and in particular is equal to the proposed value $Cond_{prop}$) and the second term is function of the second parameter The second term has a positive value since it takes into account the too low plasma conductivity/sodium concentration in blood.

With respect to diabetic patients, i.e. patients who may have a high glucose concentration value in the blood when coming in for the treatment, a conductivity adjustment may be taken into consideration, too.

As previously mentioned, the control unit 12 obtains (i.e. receives as an input or calculates) a value for a second and/or a third parameter and determines a set value $Cond_{set}$ for the first parameter as a function of the proposed value $Cond_{prop}$ for the first parameter and at least one of the second and third parameter.

In this respect, the third parameter is related to the non-ionic substance concentrations. In detail the third parameter is chosen in the group including a non-ionic substance concentration in the patient or a concentration-related parameter of at least a non-ionic substance in the patient. The non-ionic substance may be glucose.

The control unit 12 may be configured to determine the set value $Cond_{set}$ for the first parameter as a weighted function of the third parameter:

$$Cond_{set} = \beta_2 \cdot g_{conc} + \text{offset} \qquad (12)$$

optionally $\beta_2$ is a constant.

In more detail, the control unit 12 may be configured to determine the set value $Cond_{set}$ for the first parameter according to the following mathematical relationship:

$$Cond_{set} = Cond_{prop} + \beta_2 \cdot g_{conc} + \text{offset} \qquad (13)$$

wherein $Cond_{prop}$ is the proposed value for the first parameter for the dialysis fluid in the dialysis supply line 8. The offset may be or may be not present.

Accepted scientific literature states a figure of 1.35 mmol/L lower sodium for each 1 g/L of glucose.

In case the first parameter $Cond_{set}$ is actually a substance concentration (the sodium set point—mmol/l), the value of $\beta_2$ would then be included in the range between 0 and 2 mmol/L per g/L of glucose and more in detail between 0.5 and 1.5 mmol/L per g/L of glucose. In particular, a value proposed by the dialysis machine for $\beta_2$ might then be around 1.35 mmol/L per g/L of glucose.

In case the first parameter $Cond_{set}$ is actually the conductivity, the values would be around 10 times lower. In case of conductivity adjustment, then $\beta_2$ would be included in the range between zero and 0.2 mS/cm per g/L of glucose or more specifically from 0.05 to 0.15. In particular, a value proposed by the dialysis machine for $\beta_2$ might then be around 0.135 mS/cm per g/L of glucose.

In case both the second and the third parameters are taken into account for the first parameter adjustment, the control unit 12 may be configured to determine the set value $Cond_{set}$ for the first parameter according to anyone of the following mathematical relationships:

$$Cond_{set} = Cond_{prop} + \beta_1 \cdot UF \text{ volume} + \beta_2 \cdot g_{conc} + \text{offset} \qquad (14)$$

$$Cond_{set} = Cond_{prop} + \beta_1 \cdot WL + \beta_2 \cdot g_{conc} + \text{offset} \qquad (15)$$

$$\text{Cond}_{set} = \text{Cond}_{prop} + \beta_1 \cdot \text{UFvolume}/W + \beta_2 \cdot g_{conc} + \text{offset} \quad (16)$$

$$\text{Cond}_{set} = \text{Cond}_{prop} + \beta_1 \cdot \text{WL}/W + \beta_2 \cdot g_{conc} + \text{offset} \quad (17)$$

wherein $\text{Cond}_{prop}$ is the proposed value for the first parameter for the dialysis fluid in the dialysis supply line; UF volume is the ultrafiltration volume, WL is the weight loss and $\beta_1$ and $\beta_2$ are respective constants (as previously described). The offset may be or may be not present.

In these embodiments, the control unit 12 is configured to determine the set value $\text{Cond}_{set}$ for the first parameter as an algebraic sum of at least a first term, a second term and a third term: the first term is function of the proposed value $\text{Cond}_{prop}$ (and in particular is equal to the proposed value $\text{Cond}_{prop}$), the second term is function of the second parameter, the third term is function of the third parameter.

The second and the third terms have both a positive value since they take into account the too low plasma conductivity/sodium concentration in blood due to patient fluid overload and high glucose concentration in blood.

Of course different functions (e.g. nonlinear functions) may be alternatively used for the above described concentration or conductivity adjustment.

Additionally, the adjustment to take into account of fluid overload and/or glucose concentration may be applied to the whole range of proposed value for the first parameter or, alternatively, the adjustment may be applied only in case the proposed values are outside normal ranges for the first parameter.

For example, in case of sodium set point, the adjustment for fluid overload and/or glucose concentration may be applied if the proposed set point value for sodium is outside a 'normal' range for sodium concentration, e.g. sodium concentration ≤135 mM/l or sodium concentration ≥145 mM/L.

Also a single term correcting for both fluid overload and non-ionic substance concentration in blood may be used.

Once the set value $\text{Cond}_{set}$ for the first parameter is calculated, the same set value is stored in a memory and proposed (e.g. visualized) to the operator.

The operator may then manually set the value for the first parameter or confirm to the apparatus that the set value $\text{Cond}_{set}$ is acceptable and has to be set as a prescription value.

Of course, the operator confirmation may be optional and the control unit 12 may use the set value $\text{Cond}_{set}$ for properly and automatically driving the apparatus.

In this respect, the control unit 12 drives the regulating means 10 for regulating the conductivity or the concentration of the substance in the fresh dialysis fluid and sets the parameter value for the dialysis fluid in the dialysis fluid supply line 8 at the calculated set point (set value $\text{Cond}_{set}$).

In particular, the control unit 12 may be programmed to allow selection of at least one treatment mode chosen in the group including isotonic dialysis, isonatremic dialysis and isonatrikalemic dialysis, the control unit configured to drive the regulating means as a function of the calculated set value $\text{Cond}_{set}$ and of the chosen treatment mode to set either a desired dialysis fluid inlet conductivity or a desired dialysis fluid inlet substance (e.g. sodium) concentration.

Furthermore, the control unit 12 may be programmed to keep the desired dialysis fluid inlet conductivity (and/or sodium concentration) substantially constant throughout the remainder of the treatment.

Hence, the output of the described task is a new value for conductivity in the dialysis fluid, which is used as conductivity set value for the regulating means (i.e. concentrate dosing system) when (e.g. isotonic) dialysis is active.

Advantageously, the changes to sodium set value will not affect the bicarbonate set value, which remains the one set by the operator.

After the setting of the adjusted sodium set point for the (e.g. isotonic) treatment, the plasma conductivity may be further calculated/monitored using common procedures, such as those described in patents EP 547025 or in EP 920877 to monitor PC throughout the treatment.

The invention claimed is:

1. An apparatus for extracorporeal blood treatment comprising:
    a filtration unit having a primary chamber and a secondary chamber separated by a semi-permeable membrane;
    a blood withdrawal line connected to an inlet of the primary chamber;
    a blood return line connected to an outlet of the primary chamber, said blood lines being for connection to a patient cardiovascular system;
    a dialysis supply line connected to an inlet of the secondary chamber;
    a dialysis effluent line connected to an outlet of the secondary chamber;
    a producer for preparing a dialysis fluid connected to said supply line and including a regulator for regulating the composition of the dialysis fluid;
    a control unit connected to the regulator and programmed for:
        obtaining a proposed value ($\text{Cond}_{prop}$) of a first parameter for the dialysis fluid in the dialysis supply line, the first parameter being one of a conductivity of the dialysis fluid and a concentration of at least one ionic substance in the dialysis fluid, wherein said proposed value ($\text{Cond}_{prop}$) for the first parameter includes the ionic substance concentration set point or a conductivity set point for running an isotonic dialysis, isonatremic dialysis or isonatrikalemic dialysis,
        obtaining a value for a second parameter indicative of a patient fluid overload, and/or obtaining a value for a third parameter, the third parameter being a non-ionic substance concentration in the patient, and
        determining a set value ($\text{Cond}_{set}$) for the first parameter as a function of the proposed value ($\text{Cond}_{prop}$) for the first parameter and at least one of the second and third parameter.

2. The apparatus according to claim 1, wherein the second parameter is selected from the group consisting of:
    a weight loss for the patient;
    a weight loss-related parameter;
    a weight loss rate for the patient;
    an ultrafiltration volume;
    an ultrafiltration volume-related parameter;
    an ultrafiltration rate;
    an absolute blood volume;
    a ratio between an absolute blood volume and a weight of the patient;
    a relative blood volume variation
    a refilling index for the patient;
    a ratio between a weight loss for the patient and a weight of the patient;
    a ratio between an ultrafiltration volume and a weight of the patient;
    a difference between an overloaded weight of the patient and a non-overloaded weight for the patient.

3. The apparatus according to claim 1, wherein the third parameter is one of a glucose concentration ($g_{conc}$) in the patient and a concentration-related parameter of at least glucose in the patient.

4. The apparatus according to claim 1, wherein the control unit is configured to determine the set value ($Cond_{set}$) for the first parameter as a linear function of at least one of the second parameter and the third parameter.

5. The apparatus according to claim 1, wherein the control unit is configured to determine the set value ($Cond_{set}$) for the first parameter as a weighted function of the second parameter according to the following mathematical relation:

$$Cond_{set} = Cond_{prop} + \beta_1 \cdot \text{second parameter} + \text{offset},$$

wherein $\beta_1$ and offset are respective constants.

6. The apparatus according to claim 1, wherein the control unit is configured to determine the set value ($Cond_{set}$) for the first parameter as a weighted function of the third parameter:

$$Cond_{set} = Cond_{prop} + \beta_2 \cdot \text{third parameter} + \text{offset},$$

wherein $\beta_2$ and offset are respective constants.

7. The apparatus according to claim 1, wherein the control unit is configured to determine the set value ($Cond_{set}$) for the first parameter as a function of the second and the third parameter, according to the following mathematical relationship:

$$Cond_{set} = Cond_{prop} + \beta_1 \cdot \text{second parameter} + \beta_2 \cdot \text{third parameter} + \text{offset},$$

wherein $\beta_1$ and $\beta_2$ are respective constants, and wherein the offset is an additional constant.

8. The apparatus according to claim 1, wherein the control unit is configured to determine the set value ($Cond_{set}$) for the first parameter as an algebraic sum of at least one first term and one second term, the first term being function of the proposed value ($Cond_{prop}$), the second term being function of at least one of the second and third parameter.

9. The apparatus according to claim 1, wherein the control unit being configured to determine the set value ($Cond_{set}$) as an algebraic sum of at least three terms, the first term being function of the proposed value ($Cond_{prop}$), the second term being function of at least one of the second and third parameter, the third term being function of the other of said second and third parameter.

10. The apparatus according to claim 1, wherein the first parameter is the conductivity for the dialysis fluid in the dialysis supply line.

11. The apparatus according to claim 1, wherein the first parameter is a sodium concentration in the dialysis fluid in the dialysis supply line.

12. The apparatus according to claim 1, wherein the second parameter is one of a ratio between the weight loss for the patient and a weight of the patient and a ratio between an ultrafiltration volume and a weight of the patient.

13. The apparatus according to claim 1, wherein the third parameter is the glucose concentration ($g_{conc}$) in the patient.

14. The apparatus according to claim 1, wherein the control unit is configured to determine the set value ($Cond_{set}$) for the first parameter according to any of the following mathematical relationships:

$$Cond_{set} = Cond_{prop} + \beta_1 \cdot \frac{UFvolume}{W} + \beta_2 \cdot g_{conc} + \text{offset},$$

$$Cond_{set} = Cond_{prop} + \beta_1 \cdot \frac{WL}{W} + \beta_2 \cdot g_{conc} + \text{offset},$$

$$Cond_{set} = Cond_{prop} + \beta_1 \cdot WL + \beta_2 \cdot g_{conc} + \text{offset},$$

$$Cond_{set} = Cond_{prop} + \beta_1 \cdot UF\text{ volume} + \beta_2 \cdot g_{conc} + \text{offset},$$

wherein $Cond_{prop}$ is the proposed value for the first parameter for the dialysis fluid in the dialysis supply line;

UF volume is the ultrafiltration volume;

WL is the weight loss;

W is the weight of the patient;

$g_{conc}$ is the glucose concentration;

offset is a constant;

$\beta_1$ is a constant; and $\beta_2$ is a constant.

15. The apparatus according to claim 14, wherein $\beta_1$ is a constant chosen in the range:

0 to 0.3: $0 < \beta_1 < 0.3$, if the first parameter is conductivity and the second parameter is WL, the $\beta_1$ unit being mS/cm/kg;

0 to 3: $0 < \beta_1 < 3$, if the first parameter is concentration and the second parameter is WL, the $\beta_1$ unit being mmol/L/kg;

0 to 25: $0 < \beta_1 < 25$, if the first parameter is conductivity and the second parameter is WL/W, the $\beta_1$ unit being mS/cm;

0 to 250: $0 < \beta_1 < 250$, if the first parameter is concentration and the second parameter is WL/W, the $\beta_1$ unit being mmol/L; and wherein $\beta_2$ is a constant chosen in the range:

0 to 0.2: $0 < \beta_2 < 0.2$, if the first parameter is conductivity, the $\beta_2$ unit being $$\frac{mS/cm}{[g/L]};$$

or 0 to 2: $0 < \beta_2 < 2$, if the first parameter is concentration, the $\beta_2$ unit being $$\frac{mmol}{[g]}.$$

16. The apparatus according to claim 1, wherein the control unit drives the regulator for regulating one of the conductivity and the concentration of at least one substance in the dialysis fluid, the control unit setting the first parameter value for the dialysis fluid in the dialysis supply line at the set value ($Cond_{set}$) of the first parameter calculated by the control unit.

17. The apparatus according to claim 16, wherein the control unit is programmed to receive selection of at least one treatment mode chosen in the group including isotonic dialysis, isonatremic dialysis and isonatrikalemic dialysis, the control unit being configured to drive the regulator as a function of the calculated set value ($Cond_{set}$) and of the chosen treatment mode.

18. The apparatus according to claim 1, wherein the control unit is configured for either calculating the proposed value ($Cond_{prop}$) for the first parameter or receiving the proposed value ($Cond_{prop}$) as an input.

19. The apparatus according to claim 1, wherein the control unit is configured for calculating the proposed value ($Cond_{prop}$) for the first parameter as a function of a main contribution term and an adjustment contribution term, wherein the main contribution term is based on one of a plasma conductivity, a plasma conductivity-related parameter, a concentration of at least a substance in the blood, and a concentration-related parameter of at least a substance in the blood, and wherein the adjustment contribution term is based on a concentration of at least one substance in the dialysis fluid, the substance in the dialysis fluid being one of bicarbonate, potassium, acetate, lactate, citrate, magnesium, calcium, sulphate and phosphate.

20. The apparatus according to claim 19, wherein the control unit is configured to calculate a plasma conductivity as a function of: (i) the dialysate flow rate at the outlet of the secondary chamber, (ii) the blood flow rate in the blood lines, (iii) at least an initial conductivity of the dialysate, and (iv) at least one conductivity of the dialysis fluid in the dialysis supply line.

21. The apparatus according to claim 20, wherein the control unit is configured to calculate a plasma conductivity according to the following formula:

$$\kappa'_{p,1} = \kappa_{0,do} + \frac{Q_{do}}{Q_{Bset}}(\kappa_{0,do} - \kappa_{0,di}),$$

wherein:

| | |
|---|---|
| $\kappa_{p,1}$ | Plasma conductivity first estimate; |
| $Q_{do}$ | Dialysate flow rate at the filtration unit outlet; |
| $Q_{bset}$ | Set blood flow rate or set blood water flow rate at the filtration unit inlet; |
| $k_{0,di}$ | Dialysis fluid conductivity at the filtration unit inlet for a pure electrolyte solution; |
| $k_{0,do}$ | Dialysate conductivity at the filtration unit outlet for a pure electrolyte solution; |

22. An apparatus for extracorporeal blood treatment comprising:
a filtration unit having a primary chamber and a secondary chamber separated by a semi-permeable membrane;
a blood withdrawal line connected to an inlet of the primary chamber;
a blood return line connected to an outlet of the primary chamber, said blood lines being configured for connection to a patient cardiovascular system;
a dialysis supply line connected to an inlet of the secondary chamber;
a dialysis effluent line connected to an outlet of the secondary chamber;
a producer for preparing a dialysis fluid connected to said supply line and including a regulator for regulating the composition of the dialysis fluid; and
a control unit connected to the regulator and programmed to:
obtain a proposed value ($Cond_{prop}$) of a first parameter for the dialysis fluid in the dialysis supply line, the first parameter being one of a conductivity for the dialysis fluid, a conductivity-related parameter for the dialysis fluid, a concentration of at least one substance for the dialysis fluid, a concentration-related parameter of at least one substance for the dialysis fluid;
obtain a value for a second parameter, the second parameter being related to a patient fluid overload; and
determine a set value ($Cond_{set}$) for the first parameter as a function of the proposed value ($Cond_{prop}$) for the first parameter and the second parameter, wherein the control unit is configured to determine the set value ($Cond_{set}$) for the first parameter as a function of the second parameter according to the following mathematical relationship:

$Cond_{set} = Cond_{prop} + \beta_1 \cdot \text{second parameter} + \text{offset},$ wherein $Cond_{prop}$ is the proposed value for the first parameter for the dialysis fluid in the dialysis supply line, β1 and offset being respective constants.

23. The apparatus according to claim 19, wherein the control unit is configured to calculate a plasma conductivity as a function of: (i) the dialysate flow rate at the outlet of the secondary chamber, (ii) at least one efficiency parameter of the filtration unit, (iii) at least one initial conductivity of the dialysate, and (iv) at least one conductivity of the dialysis fluid in the dialysis supply line.

24. The apparatus according to claim 19, wherein the control unit is configured to calculate a plasma conductivity according to the following formula:

$$\kappa''_{p,1} = \kappa_{0,di} + \frac{Q_{do}}{K_u}(\kappa_{0,do} - \kappa_{0,di}),$$

wherein:

| | |
|---|---|
| $K_{p,1}$ | Plasma conductivity first estimate; |
| $Q_{do}$ | Dialysate flow rate at the filtration unit outlet; |
| $K_u$ | Filtration unit clearance for urea; |
| $k_{0,di}$ | Dialysis fluid conductivity at the filtration unit inlet for a pure electrolyte solution; |
| $k_{0,do}$ | Dialysate conductivity at the filtration unit outlet for a pure electrolyte solution; |

25. An apparatus for extracorporeal blood treatment comprising:
a filtration unit including a primary chamber and a secondary chamber separated by a semi-permeable membrane;
a blood withdrawal line connected to an inlet of the primary chamber;
a blood return line connected to an outlet of the primary chamber, said blood lines configured for connection to a patient cardiovascular system;
a dialysis supply line connected to an inlet of the secondary chamber;
a dialysis effluent line connected to an outlet of the secondary chamber;
a producer for preparing a dialysis fluid connected to said supply line and including a regulator for regulating the composition of the dialysis fluid; and
a control unit connected to the regulator and programmed to:
obtain a proposed value ($Cond_{prop}$) of a first parameter for the dialysis fluid in the dialysis supply line, the first parameter being one of a conductivity for the dialysis fluid, a conductivity-related parameter for the dialysis fluid, a concentration of at least one ionic substance for the dialysis fluid, a concentration-related parameter of at least one ionic substance for the dialysis fluid,
obtain a value for a third parameter, the third parameter being a non-ionic substance concentration in the patient, and
determine a set value ($Cond_{set}$) for the first parameter as a function of the proposed value ($Cond_{prop}$) for the first parameter and the third parameter.

26. The apparatus of claim 25, wherein the control unit is configured to determine the set value ($Cond_{set}$) for the first parameter as a function of the third parameter according to the following mathematical relationship:

$$Cond_{set} = Cond_{prop} + \beta_2 \cdot \text{third parameter} + \text{offset}$$

wherein $Cond_{prop}$ is the proposed value for the first parameter for the dialysis fluid in the dialysis supply line, and wherein β2 and offset are respective constants.

27. An apparatus for extracorporeal blood treatment comprising:
a filtration unit including a primary chamber and a secondary chamber separated by a semi-permeable membrane;
a blood withdrawal line connected to an inlet of the primary chamber;
a blood return line connected to an outlet of the primary chamber, said blood lines configured for connection to a patient cardiovascular system;
a dialysis supply line connected to an inlet of the secondary chamber;
a dialysis effluent line connected to an outlet of the secondary chamber;
a producer for preparing a dialysis fluid connected to said supply line and including a regulator for regulating the composition of the dialysis fluid; and
a control unit connected to the regulator and programmed to:
calculate a proposed value ($Cond_{prop}$) of a first parameter for the dialysis fluid in the dialysis supply line, the first parameter being one of a conductivity of the dialysis fluid and a concentration of at least one ionic substance in the dialysis fluid, wherein calculating the proposed value ($Cond_{prop}$) is function of a main contribution term and an adjustment contribution term,
wherein the main contribution term is based on one of a plasma conductivity, a plasma conductivity-related parameter, a concentration of at least one ionic substance in the blood, and a concentration-related parameter of at least one ionic substance in the blood, and
wherein the adjustment contribution term is based on a concentration of at least one substance in the dialysis fluid, the substance in the dialysis fluid being one of bicarbonate, potassium, acetate, lactate, citrate, magnesium, calcium, sulphate and phosphate,
obtain a value for a second parameter indicative of a patient fluid overload,
obtain a value for a third parameter, the third parameter being a non-ionic substance concentration in the patient, and
determine a set value ($Cond_{set}$) for the first parameter as a function of the proposed value ($Cond_{prop}$) for the first parameter and at least one of the second and third parameter.

28. An apparatus for extracorporeal blood treatment comprising:
a filtration unit including a primary chamber and a secondary chamber separated by a semi-permeable membrane;
a blood withdrawal line connected to an inlet of the primary chamber;
a blood return line connected to an outlet of the primary chamber, said blood lines being configured for connection to a patient cardiovascular system;
a dialysis supply line connected to an inlet of the secondary chamber;
a dialysis effluent line connected to an outlet of the secondary chamber;
a producer for preparing a dialysis fluid connected to said supply line and including a regulator for regulating the composition of the dialysis fluid; and
a control unit connected to the regulator and programmed to:
obtain a proposed value ($Cond_{prop}$) of a first parameter for the dialysis fluid in the dialysis supply line, the first parameter being one of a conductivity of the dialysis fluid and a concentration of at least one ionic substance in the dialysis fluid,
obtain a value for a second parameter indicative of a patient fluid overload,
obtain a value for a third parameter, the third parameter being a non-ionic substance concentration in the patient, and
determine a set value ($Cond_{set}$) for the first parameter as a function of the proposed value ($Cond_{prop}$) for the first parameter according to any of the following mathematical relationships:

$$Cond_{set} = Cond_{prop} + \beta_1 \cdot WL + \beta_2 \cdot g_{conc} + \text{offset},$$

$$Cond_{set} = Cond_{prop} + \beta_1 \cdot \frac{WL}{W} + \beta_2 \cdot g_{conc} + \text{offset},$$

wherein
$Cond_{prop}$ is the proposed value for the first parameter for the dialysis fluid in the dialysis supply line,
UF volume is the ultrafiltration volume,
WL is the weight loss,
W is the weight of the patient,
$g_{conc}$ is the glucose concentration,
offset is a constant,
$\beta_1$ is a constant chosen in the range:
0 to 0.3: $0 < \beta_1 < 0.3$, if the first parameter is conductivity and the second parameter is WL, the $\beta_1$ unit being mS/cm/kg,
0 to 3: $0 < \beta_1 < 3$, if the first parameter is concentration and the second parameter is WL, the $\beta_1$ unit being mmol/L/kg,
0 to 25: $0 < \beta_1 < 25$, if the first parameter is conductivity and the second parameter is WL/W, the $\beta_1$ unit being mS/cm, and
0 to 250: $0 < \beta_1 < 250$, if the first parameter is concentration and the second parameter is WL/W, the $\beta_1$ unit being mmol/L, and
$\beta_2$ is a constant chosen in the range:
0 to 0.2: $0 < \beta_2 < 0.2$, if the first parameter is conductivity, the $\beta_2$ unit being $$\left[\frac{mS/cm}{g/L}\right],$$

and 0 to 2: $0 < \beta_2 < 2$, if the first parameter is concentration, the $\beta_2$ unit being $$\left[\frac{mmol}{g}\right].$$

* * * * *